US010796463B2

(12) United States Patent
Langan et al.

(10) Patent No.: US 10,796,463 B2
(45) Date of Patent: Oct. 6, 2020

(54) TOMOGRAPHIC IMAGING FOR TIME-SENSITIVE APPLICATIONS

(71) Applicant: GENERAL ELECTRIC COMPANY, Schenectady, NY (US)

(72) Inventors: David Allen Langan, Clifton Park, NY (US); Bernhard Erich Hermann Claus, Niskayuna, NY (US); Gregoire Avignon, New York, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 295 days.

(21) Appl. No.: 14/819,192

(22) Filed: Aug. 5, 2015

(65) Prior Publication Data
US 2017/0039734 A1 Feb. 9, 2017

(51) Int. Cl.
*G06T 11/00* (2006.01)
*A61B 6/03* (2006.01)
*A61B 6/00* (2006.01)

(52) U.S. Cl.
CPC ............ *G06T 11/003* (2013.01); *A61B 6/032* (2013.01); *A61B 6/481* (2013.01); *A61B 6/486* (2013.01); *A61B 6/507* (2013.01); *G06T 2211/424* (2013.01)

(58) Field of Classification Search
CPC . G06T 11/003; G06T 2211/424; A61B 6/032; A61B 6/481; A61B 6/486; A61B 6/507
See application file for complete search history.

(56) References Cited

U.S. PATENT DOCUMENTS

| 6,556,695 B1 | 4/2003 | Packer et al. |
|---|---|---|
| 8,023,616 B2 | 9/2011 | Boese |
| 8,335,557 B2 | 12/2012 | Maschke |

(Continued)

FOREIGN PATENT DOCUMENTS

| DE | 102011083703 A1 | 4/2013 |
|---|---|---|
| DE | 102011083708 A1 | 4/2013 |

(Continued)

OTHER PUBLICATIONS

Mistretta, "Sub-Nyquist acquisition and constrained reconstruction in time resolved angiography.", Med Phys, vol. 38, Issue 6, pp. 2975-2985, 2011.

(Continued)

*Primary Examiner* — Courtney D Thomas
(74) *Attorney, Agent, or Firm* — Fletcher Yoder, P.C.

(57) ABSTRACT

Disclosed aspects relate to the acquisition and processing of projection data using temporal characteristics of the imaged volume, such as the uptake and clearance of a contrast agent within the volume. Such temporal aspects may be used in the acquisition process, such as to differentially acquire images based on the propagation of the contrast agent. In addition, such temporal aspects may be used in the processing of projection data to generate differential projections (e.g., first or second order subtraction projections), compound projections synthesized using the absolute or relative maximum opacity values observed over time for a region of interest, or interpolated projections synthesized using observed opacity values at known or fixed time intervals and a derived peak opacity time.

21 Claims, 9 Drawing Sheets

(56) References Cited

U.S. PATENT DOCUMENTS

| | | |
|---|---|---|
| 8,386,019 B2 | 2/2013 | Camus et al. |
| 8,643,642 B2 | 2/2014 | Mistretta et al. |
| 86,541,199 | 2/2014 | Mistretta et al. |
| 8,855,391 B2 | 10/2014 | Boese |
| 9,047,685 B2 | 6/2015 | Goel et al. |
| 2007/0027390 A1 | 2/2007 | Maschke et al. |
| 2013/0046176 A1* | 2/2013 | Mistretta ............... A61B 6/032 600/431 |
| 2013/0303884 A1 | 11/2013 | Kuntz et al. |

FOREIGN PATENT DOCUMENTS

| | | |
|---|---|---|
| WO | 2008150945 A2 | 12/2008 |
| WO | 2011022336 A2 | 2/2011 |
| WO | 2012084726 A1 | 6/2012 |

OTHER PUBLICATIONS

Fieselmann et al., "Interventional 4-D C-Arm CT Perfusion Imaging Using Interleaved Scanning and Partial Reconstruction Interpolation", Medical Imaging, IEEE Transactions on, vol. 31, Issue 4, pp. 892-906, Dec. 23, 2011.

Kagadis et al., "Emerging technologies for image guidance and device navigation in interventional radiology:", Medical Physics, vol. 39, 2012.

Kuntz et al., "Real-time X-ray-based 4D image guidance of minimally invasive interventions", Eur Radiol, vol. 23, Issue 6, pp. 1669-1677, 2013.

Manhart et al., "Dynamic Iterative Reconstruction for Interventional 4-D C-Arm CT Perfusion Imaging", Medical Imaging, IEEE Transactions on, vol. 32, Issue 7, pp. 1-14, Apr. 5, 2013.

\* cited by examiner

TOMOGRAPHIC IMAGING FOR TIME-SENSITIVE APPLICATIONS

BACKGROUND

The subject matter disclosed herein relates to imaging techniques in which data of interest may occur at different times in the procedure, such as due to different physiological processes or as part of an interventional or navigational procedure.

Various medical procedures involve the insertion and navigation of a tool within a patient's body. For example, needle-based procedures (e.g., lung biopsy, vertebroplasty, RF ablation of liver tumors, and so forth) may involve the insertion and navigation of a needle or needle associated tool through the body of a patient. Endovascular procedures involve navigation and positioning of catheters and other devices, generally within the vasculature of the patient. Certain of these procedures involve the delivery of a treatment, such as a drug or other agent, to a particular location within the body and may benefit from timely and accurate internal images. Such procedures are guided and, therefore, benefit from the acquisition and display of imaging data to assist in the navigation process. In some procedures, contrast agents and/or other agents (e.g., drugs) are delivered through intravenous or intra-arterial injection, and the user may benefit from viewing data displaying the temporal evolution of the propagation of the agent through the vasculature and/or the tissue.

Such image data may be acquired using imaging modalities that employ various radiological principles. For example, technologies such as X-ray fluoroscopy, X-ray computed tomography (CT), and tomosynthesis use the varying transmission of X-rays through a target volume to acquire projection data and to construct images (e.g., three-dimensional, volumetric representations of the interior of the human body or of other imaged structures).

As part of such procedures, a contrast agent may be administered which may facilitate the visualization of one or both of the vasculature and/or the anatomic structures of interest. Various issues may complicate such contrast-enhanced image acquisitions, however. For example, for a given bolus of contrast, the contrast may pass through different structures of interest at different times or rates, making acquisition, visualization and use of the temporally-differentiated image information difficult. By way of example, in instances where the propagation of the contrast through different anatomic regions occurs over an extended period (e.g., a minute or more), at any given moment, only a subset of the vasculature or structures of interest are fully opacified. Thus, one feature of interest may be decreasing in visibility while other are just attaining full visibility, or perhaps have not even begun to be opacified. In addition, not only the 3D structure of the features of interest, but also the temporal evolution of the contrast uptake and washout may provide valuable information to the clinician.

BRIEF DESCRIPTION

In one embodiment, a method of acquiring X-ray projection data is provided. In accordance with this method, an X-ray source and an X-ray detector of a tomographic imaging system are moved within a limited angular range with respect to an imaged volume. The X-ray source is constrained to move on a first side of the imaged volume and the X-ray detector is constrained to move on a second side of the imaged volume opposite the first side. Prior to an event of interest, projection data is at one or more of a first frame rate, a first operating current, a first operating voltage, or a first field-of-view using the X-ray source and the X-ray detector while moving the X-ray source and the X-ray detector through one or more orbits. Subsequent to the event of interest, projection data is acquired at one or more of a second frame rate, a second operating current, a second operating voltage, or a second field-of-view using the X-ray source and the X-ray detector while moving the X-ray source and the X-ray detector through the one or more orbits. Threshold distances, sampling rates, effective dose values and so forth may be driven by application or examination specific considerations. For example, in certain implementations, one or more of dose to a patient, frame rate, and/or angular coverage may be reduced or minimized when watching bolus progression toward a region-of-interest (e.g., low frame rate, two-dimensional imaging). As the bolus approaches the region-of-interest, however, one or more of dose, frame rate, and/or angular coverage may be increased, such as to achieve high frame rate, three-dimensional imaging.

In a further embodiment, a method of processing projections is provided. In accordance with this method, an X-ray source and an X-ray detector of a tomographic imaging system are moved within a limited angular range along an orbital path with respect to an imaged volume. The X-ray source is constrained to move on a first side of the imaged volume and the X-ray detector is constrained to move on a second side of the imaged volume opposite the first side. Projection data is acquired using the X-ray source and the X-ray detector while moving the X-ray source and the X-ray detector in the orbital path and relative to the imaged anatomy. The acquisition of projection data yields projection images of the imaged anatomy in two or more states. One or more three-dimensional images adapted to the dynamic nature of the imaged object are generated. The generating of the three-dimensional images is adapted based on one or more of selection of a time window for reconstruction, generation or use of compound or interpolated projections, separate reconstruction of structures within the three-dimensional images, or temporal evolution of at least one category of structure. In certain embodiments, the resulting three-dimensional representation of, for example, contrast dynamics within the vasculature, may occur on a faster time-scale than, for example the acquisition (e.g., the orbit time).

In an additional embodiment, a method of generating a compound projection is provided. In accordance with this method, an X-ray source and an X-ray detector of a tomographic imaging system are moved within a limited angular range along an orbital path with respect to an imaged volume. The X-ray source is constrained to move on a first side of the imaged volume and the X-ray detector is constrained to move on a second side of the imaged volume opposite the first side. Projection data is acquired using the X-ray source and the X-ray detector while moving the X-ray source and the X-ray detector in the orbital path and relative to the patient table. At least a set of projections are acquired at the same view angle at different times. For one or more pixels of interest depicted in the set of projections, a pixel value corresponding to a maximum X-ray attenuation among two or more projections of the set of projections is determined. A compound projection is generated using the pixel values for the pixels of interest.

In another embodiment, a method of generating an interpolated projection is provided. In accordance with this method, an X-ray source and an X-ray detector of a tomographic imaging system are moved within a limited angular range along an orbital path with respect to an imaged volume. The X-ray source is constrained to move on a first side of the imaged volume and the X-ray detector is constrained to move on a second side of the imaged volume opposite the first side. Projection data is acquired using the X-ray source and the X-ray detector while moving the X-ray source and the X-ray detector in the orbital path and relative to the patient table. At least a set of projections are acquired at the same view angle at different times. A time of interest is determined for each of one or more pixels of interest depicted in the set of projections. Based on the time of interest for each pixel of interest, an interpolated intensity is determined for each pixel of interest using two or more respective projections from the set of projections. An interpolated projection is generated using the interpolated intensities for the pixels of interest.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
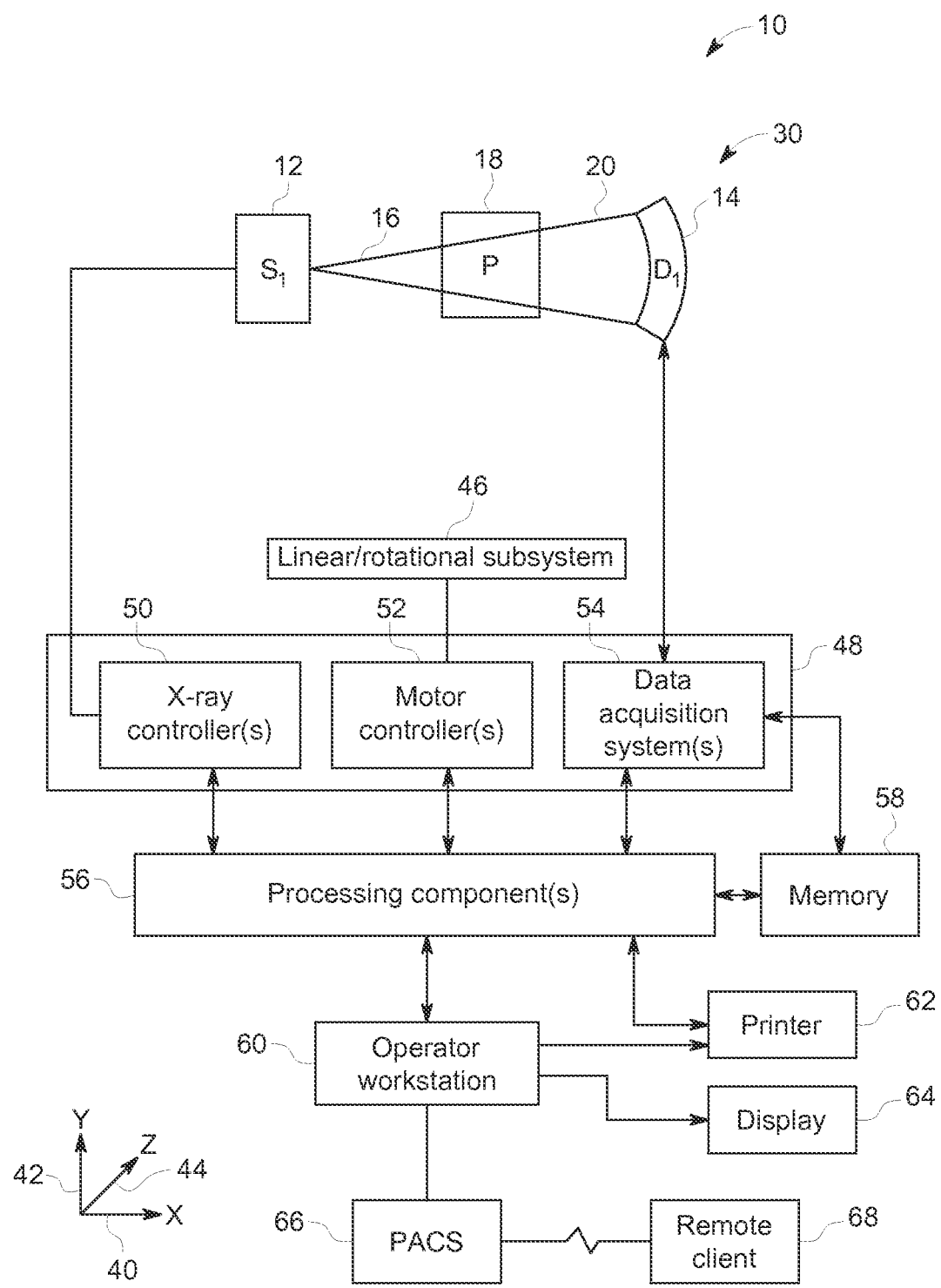
FIG. 1 is a diagrammatical view of an imaging system for use in producing images in accordance with aspects of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

In certain imaging procedures (including procedures using an interventional C-arm or similar system), it is useful to be able to visualize the internal structures of a patient as part of the procedure. Aspects of the present approach utilize C-arm tomosynthesis to provide such images. As discussed herein, in certain embodiments, a C-arm mounted X-ray detector and source (e.g., an X-ray tube) continuously orbit within respective planes or slabs above and below the patient support table (and/or along the lateral sides of the patient support table). As may be appreciated, in such tomosynthesis examinations an acquisition motion or trajectory may be employed having a small tomographic angle. This may be desirable to the extent it allows 3D imaging in situations where cone beam computed tomography (CBCT) and computer tomography (CT) are infeasible due to collision hazards with procedure room apparatus, patient, and/or medical staff (e.g., space and geometric constraints). In such embodiments, the operator is provided good access to the patient, in contrast to other types of imaging modalities where movement of the system components may spatially or temporally limit access to the patient.

As with other X-ray imaging modalities, to facilitate imaging of certain structures within the patient, a contrast agents may be administered to the patient for certain types of examinations. For example, such contrast agents may be administered to temporarily increase the visibility of structures that may otherwise be hard to view based on differential X-ray absorption, such as soft tissue and vasculature. Such contrast-enhancement may be particularly useful in interventional procedures, where accurate depiction of the vasculature is needed, as well as in procedures where the flow of the contrast (e.g., characteristics of contrast uptake and washout, arterial and venous phase) may convey useful diagnostic information.

Due to the nature of contrast uptake and clearance through different anatomic regions, however, the useful information that may be gleaned from the contrast agent may be obtained over differing time frames and/or with respective delays for different information, and thus may not be readily obtained at a single point in time. By way of example, accurate depiction of the arterial blood flow downstream from where a bolus is administered may be available soon after administration and for a brief interval as the contrast travels quickly through the arterial vasculature. Venous vasculature may be visible subsequent to the arterial flow and may also be visible for a brief interval, though often for slightly longer than the arterial vasculature as the transition from the arterial to the venous vasculature may introduce a certain degree of variability and lag to the time window in which the contrast enters the veins. Further, the uptake and clearance of the contrast through other structures (e.g., lesions, tumors, the parenchyma, and so forth) may be associated with yet another time frame. For example, the contrast may be relatively slow in being taken up, and cleared from, a tissue of interest, such as a lesion. As a result, the useful information (both in the 2D projection domain, as well as in a 3D volumetric reconstruction) associated with the administration of a contrast bolus may not be easily derived from a scan made at a single point in time, or even over a contiguous time interval, which might be composed of intervals where the contrast flow is of little interest interspersed with intervals where the contrast flow conveys useful information. Further, conventional systems are generally set up only to acquire either 2D data (i.e. projection data at a fixed view angle) over time, or acquire a dataset for reconstruction of a 3D volume scan at a single point in time, (or multiple, discrete and separate time points).

With this in mind, the present approach provides for approaches where the image data can be differentially acquired and/or differentially processed so as to increase the usefulness of the data acquired from a contrast enhancement procedure. In this manner, the usefulness of the data acquired and/or reconstructed from different times during contrast propagation may be maximized for a given procedure. Such approaches may facilitate not only visualization of the anatomic structures of interest, but may also allow visualization of the temporal aspects or evolution of the contrast propagation in a three-dimensional spatial context. Such information may be useful not only for diagnostic purposes, but also for interventional or navigational procedures, such as 4D (i.e., 3D plus time) device guidance.

With the preceding comments in mind, it should be appreciated that, though C-arm tomosynthesis is described herein as an example of a suitable imaging modality, such embodiments are merely described to facilitate explanation and to provide a working example. It should be appreciated that aspects of the present approach, such as those related to temporal and/or spatial data aggregation as well as the differential acquisition of data points over time, may be applicable to other acquisition approaches and imaging modalities. Thus, such examples should be understood to be non-limiting and provided only to simplify explanation by providing an example of useful implementations.

With the preceding in mind, an example of a single-plane tomosynthesis imaging system 10 suitable for acquiring X-ray attenuation data for reconstruction as discussed herein is provided in FIG. 1. As discussed herein, in certain implementations the tomosynthesis acquisition operates such that the X-ray detector and source (e.g., an X-ray tube) orbit one or more times above and below the patient. For example, the source and detector may each orbit within separate respective planes or other constrained 2D or 3D trajectories, one above and one below, the patient. In one such implementation, the orbit may have a half tomosynthesis angle of 15° to 30° (where the tomographic angle, or tomosynthesis angle is measured as the angle between the gantry angle and a reference direction) and an orbit period of 3 to 8 seconds. Relative to other imaging modalities (e.g., CBCT and computed tomography (CT)), the tomosynthesis acquisition gantry motion has a significantly reduced footprint, providing the opportunity to perform a tomosynthesis acquisition in circumstances where other imaging approaches are prohibited due to the risk of collision with procedure room apparatus, the patient, and/or staff. A continuous orbit, when employed, provides timing flexibility for the procedure and imaging operation, enabling manual contrast administration, physiologic gating, selection of the bolus delay to be reconstructed, and so forth. The present approach, however, does not require continuous or continued orbital motion of the source and detector during a procedure, though certain such continuous motion implementations will be discussed by way of example. Further, as discussed in greater detail below, even when continuous motion of the source and detector components is present, data acquisition (e.g., X-ray emission, detector readout, and so forth) may be varied (e.g., intermittent or periodic) over the course of a scan procedure. For example, X-ray emission and acquisition may be based on the image quality needs at a given time in a procedure or based upon the observed or expected propagation of contrast within the patient.

In the embodiment illustrated in FIG. 1, imaging system 10 includes a source of X-ray radiation 12 and a detector 14. The X-ray source 12 may be an X-ray tube, a distributed X-ray source (such as a solid-state or thermionic X-ray source) or any other source of X-ray radiation suitable for the acquisition of medical or other images. The X-rays 16 generated by the source 12 pass into a region in which a patient 18, is positioned during a procedure. In the depicted example, the X-rays 16 are collimated to be a cone-shaped beam, e.g., a cone-beam, which passes through the imaged volume. A portion of the X-ray radiation 20 passes through or around the patient 18 (or other subject of interest) and impacts a detector array, represented generally as the detector 14. Detector elements of the detector 14 produce electrical signals that represent the intensity of the incident X-rays 20. These signals are acquired and processed, as discussed herein, to reconstruct images of the features within the patient 18. While FIG. 1 depicts a single-plane imaging system 10, in certain embodiments the imaging system may be a bi-plane imaging system that includes an additional source of X-ray radiation and an additional detector configured to acquire projection images at a different direction, orientation, location, and/or timing than the source 12 and detector 14.

In the present example, the source 12 and detector 14 may be a part of an imager subsystem 30. As depicted, the imager 30 positions the source 12 and the detector 14, at rest, generally along a direction, which may correspond to the AP direction of the patient 18 in certain embodiments. For example, the imager 30 may acquire X-ray images or X-ray projection data over a limited angular range with respect to one side or facing (e.g., the anterior/posterior (AP) direction) of the patient 18, thereby defining data in a first plane (e.g., a frontal plane of the patient 18). In this context, an imaging plane may be defined as a set of projection directions that are located within a certain angular range relative to a reference direction. For example, the frontal imaging plane may be used to describe projection views within an angular range that is within, for example, 30 degrees of the PA (posterior/anterior) direction of the patient. Similarly, the lateral imaging plane, if imaged by the imager 30 or a second imager, may be described as the set of projection directions within an angular range that is within 30 degrees of the lateral/horizontal left/right projection direction.

In accordance with present embodiments, the imager 30 may be moved relative to the patient or imaged object along one or more axes during an examination procedure during which projection data is acquired. For example, the imager 30 may move about a first axis of rotation 40, a second axis of rotation 42, or a third axis of rotation 44, or any combination thereof. Such imager 30 motion may be supplemented by motion of the underlying patient support (e.g., table) to achieve complex imaging trajectories with respect to the relative position and motion between the imager 30 and patient over time. In one embodiment, the translation and rotation of the imager 30 may be determined or coordinated in accordance with a specified protocol.

The movement of the imager 30 may be initiated and/or controlled by one or more linear/rotational subsystems 46. The linear/rotational subsystems 46, as discussed in further detail below, may include support structures, motors, gears, bearings, and the like, that enable the rotational and/or translational movement of the imager 30. In one embodiment, the linear/rotational subsystems 46 may include a structural apparatus (e.g., a C-arm apparatus having rotational movement about at least two axes) supporting the source and detector 12, 14.

A system controller 48 may govern the linear/rotational subsystems 46 that initiate and/or control the movement of the imager 30 as well as X-ray emission and detector readout. In practice, the system controller 48 may incorporate one or more processing devices that include or communicate with tangible, non-transitory, machine readable media collectively storing instructions executable by the one or more processors to perform the operations described herein. The system controller 48 may also include features that control the timing of the activation of the sources 12, for example, to control the acquisition of X-ray attenuation data obtained during a particular imaging sequence. The system controller 48 may also execute various signal processing and filtration functions, such as for initial adjustment of dynamic ranges, interleaving of digital projection data, and so forth. Therefore, in general, the system controller 48 may be considered to command operation of the imaging system 10 to execute examination protocols. It should be noted that, to facilitate discussion, reference is made below to the system controller 48 as being the unit that controls acquisitions, movements, and so forth, using the imager. However, embodiments where the system controller 48 acts in conjunction with other control devices (e.g., other control circuitry local to the imagers or remote to the system 10) are also encompassed by the present disclosure.

In the present context, the system controller 48 includes signal processing circuitry and various other circuitry that enables the system controller 48 to control the operation of the imager 30 and the linear/rotational subsystems 46. In the illustrated embodiment, the circuitry may include an X-ray controller 50 configured to operate the X-ray source 12 so as to time the operations of the source and to interleave the acquisition of X-ray attenuation data when needed. Circuitry of the system controller 48 may also include one or more motor controllers 52. The motor controllers 52 may control the activation of various components that are responsible for moving the source 12 and the detector 14. In other words, the motor controllers may implement a particular trajectory along which components (e.g., the source 12 and detector 14) of the imager 30 move in a continuous or discontinuous manner during a scan session.

The system controller 48 is also illustrated as including one or more data acquisition systems 54. Generally, the detector 14 may be coupled to the system controller 48, and more particularly to the data acquisition systems 54. The data acquisition systems 54 may receive data collected by read out electronics of the detector 14 and in certain embodiments may process the data (e.g., by converting analog to digital signals or to perform other filtering, transformation, or similar operations).

It should be noted that the tangible, non-transitory, machine-readable media and the processors that are configured to perform the instructions stored on this media that are present in the system 10 may be shared between the various components of the system controller 48 or other components of the system 10. For instance, as illustrated, the X-ray controller 50, the motor controller 52, and the data acquisition systems 54 may share one or more processing components 56 that are each specifically configured to cooperate with one or more memory devices 58 storing instructions that, when executed by the processing components 56, perform the image acquisition and reconstruction techniques described herein. Further, the processing components 56 and the memory components 58 may coordinate in order to perform the various image reconstruction processes.

The system controller 48 and the various circuitry that it includes, as well as the processing and memory components 56, 58, may be accessed or otherwise controlled by an operator via an operator workstation 60. The operator workstation 60 may include any application-specific or general-purpose computer that may include one or more programs (for example one or more imaging programs) capable of enabling operator input for the techniques described herein, such as to modulate the X-ray emissions of the source 12 or the readout of the detector 14, select data for processing (e.g., selection of a time-window for data that is to be used in a 3D reconstruction), and so forth. The operator workstation 60 may include various input devices such as a mouse, a keyboard, a trackball, or any other similar feature that enables the operator to interact with the computer. The operator workstation 60 may enable the operator to control various imaging parameters, for example, by adjusting certain instructions stored on the memory devices 58.

The operator workstation 60 may be communicatively coupled to a printer 62 for printing images, patient data, and the like. The operator workstation 60 may also be in communication with a display 64 that enables the operator to view various parameters in real time, to view images produced by the acquired data, and the like. The operator workstation 60 may also, in certain embodiments, be communicatively coupled to a picture archiving and communication system (PACS) 66. Such a system may enable the storage of patient data, patient images, image acquisition parameters, and the like. This stored information may be shared throughout the imaging facility and may also be shared with other facilities, for example, a remote client 68. The remote client 68 may include hospitals, doctors' offices, or any other similar client.

Figure 2:
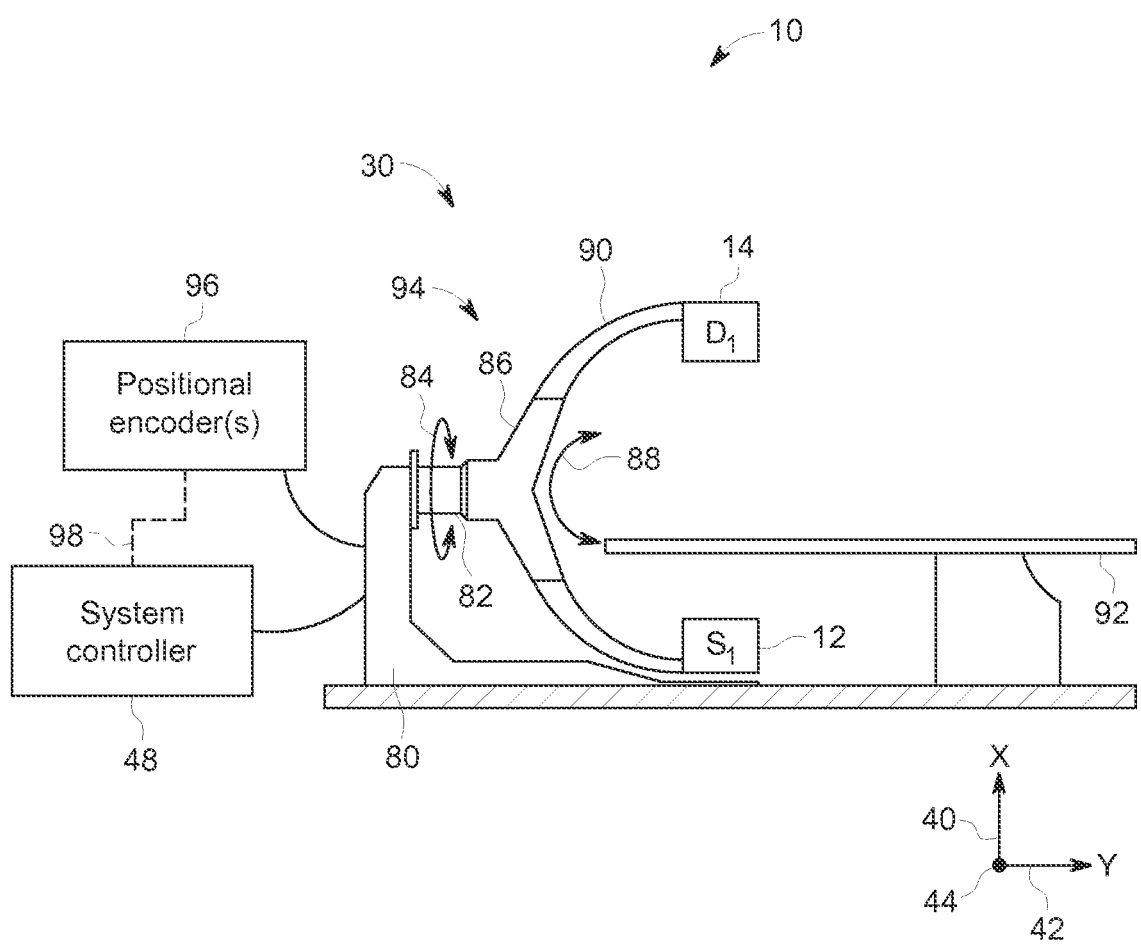
FIG. 2 is a schematic side view of an imaging system in which an imaging apparatus obtains projection data along a plane via rotation about two axes, in accordance with aspects of the present disclosure.

Various aspects of the present approaches may be further appreciated with respect to FIG. 2, which is a side view of an embodiment of the system 10. The imager 30, as illustrated, includes a base 80 and a rotatable extension 82 extending from the base 80. In the illustrated embodiment, the base 80 is a floor-mounted base such that the imager 30 may be secured to a floor of an imaging area in which it is positioned. In other embodiments, however, the base 80 may be secured to other surfaces (e.g., a wall or ceiling) and/or may be mobile or movable.

The rotatable extension 82 is depicted as extending generally along the second axis of rotation 42, and enables the source 12 and the detector 14 to move about the second axis of rotation 42. For example, the rotatable extension 82 may enable the source 12 and the detector 14, mechanically affixed to the C-arm, to move about the second axis of rotation 42 opposite one another relative to the imaged volume. The rotation enabled by the rotatable extension 82 is shown as double-headed arrow 84. The rotatable extension 82 is coupled to a moving structure 86 (e.g., directly or indirectly via an extension arm), which enables the source 12 and the detector 14 to move about the third axis of rotation 44. This rotation about the third axis of rotation 44 is depicted as double-headed arrow 88.

The moving structure 86 may be a geared or track structure that is motively coupled to a support structure 90 that physically supports the source 12 and the detector 14, and may be in the form of a C-arm, or any other shape that positions the source 12 and the detector 14 on either side of the patient 18. As illustrated, the support structure 90 includes an arcuate structure that extends from a first side of a patient table 92, around the patient table 92, and to a second side of the patient table 92. In this way, the source 12 and the detector 14 generally remain positioned at opposite ends and/or on opposite sides of the patient (not shown) positioned on patient table 92. During a procedure, in addition to the source and detector motion described above, the table 92 may be moved as well during imaging (such as linearly translated) to achieve the prescribed relative motion of patient and imager. Together, the base 80, the rotatable extension 82, the moving structure 86, and the support structure 90 may be considered to be the structure 94 of the imager 30.

The imager 30 may include various motors, actuators, or other features responsible for movement of the various structures of the imager 30, and they may be communicatively coupled to one or more positional encoders 96. The one or more positional encoders 96 may encode the respective positions of any one or more components of the imager 30 in a manner that facilitates processing by the system controller 48. In such an implementation, the positional encoders 96 may provide feedback 98 (for example via wired or wireless signals) to the system controller 48. The system controller 48 may use this feedback 98 to control the imager 30.

As an example, the system controller 48 may simultaneously move the source 12 and the detector 14 together about the first axis of rotation 40, the second axis of rotation 42, or the third axis of rotation 44, or any combination thereof, and obtain X-ray attenuation data for a subset of the traversed view angles. In one embodiment, the system controller 48 may receive positional information from the positional encoders 96 relating to the imager 30 and may calculate a trajectory (or update a modeled trajectory) for either or for both of the source and detector 12, 14 using this positional feedback information.

Furthermore, the system controller 48 may synthesize one or more volumetric images using data obtained by the imager 30. Tomosynthesis reconstruction algorithms, as discussed herein, may be used to reconstruct a 3D volumetric image of the imaged region of interest. In one such embodiment, the imager 30 may perform an acquisition of data using an acquisition trajectory (e.g., a circular, ellipsoidal, or similar path traced by the source 12 below (or above) the patient 18 and a corresponding circular, ellipsoidal, or similar path traced by the detector above (or below) the patient 18, referred to herein as a frontal tomosynthesis trajectory). An example of such a motion (i.e., an "orbit" as used herein) is conceptually demonstrated in FIG. 3 in the context of imager 30. In this example, the imager 30 may obtain projection data from a plurality of projection directions, but these projection directions may be limited by the angular range of motion of the imager 30 (e.g., the limited angular displacement about the second rotational axis 42) and/or the presence of proximate structures or personnel. In one embodiment, the angular range of the trajectory may also be limited due to temporal constraints. In one example, the angular range of an elliptical orbit that is part of the trajectory may be defined by the requirement that the orbit may have to be traversed in a certain amount of time, e.g., in 3 seconds or less.

With the preceding in mind, as used herein, a tomosynthesis trajectory of an imager may be described as a path (e.g., a line, curve, circle, oval, and so forth, as well as combinations thereof) traced by an X-ray source during image acquisition. A tomosynthesis acquisition by an imager or imager subsystem occurs over a limited angular range with respect to the patient (such as with respect to one side, e.g., the front, back, left side, or right side, of the patient), and thus a trajectory will typically move the source within this limited angular range with respect to the imaged subject.

Figure 3:
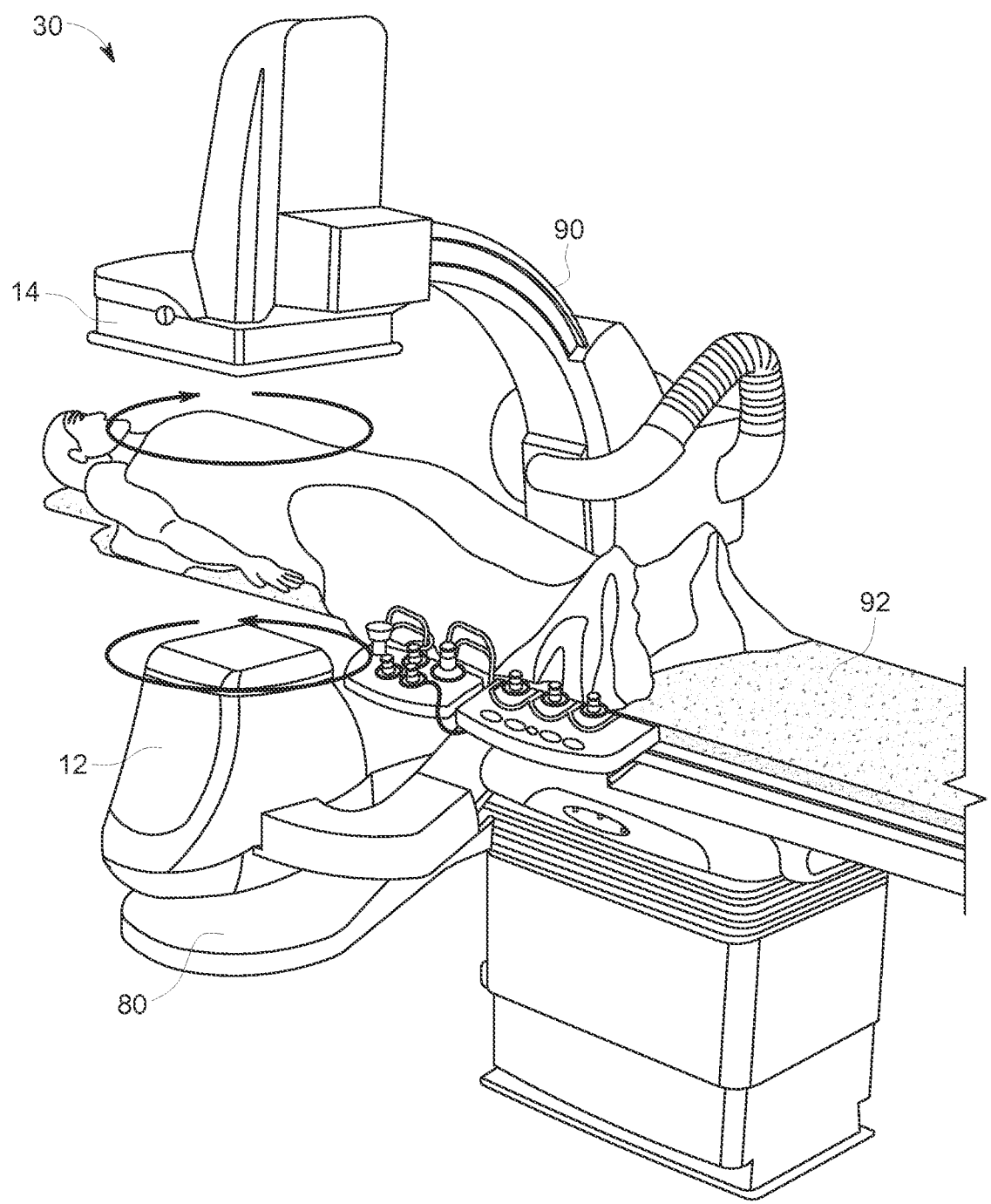
FIG. 3 depicts movement of a source and detector of a C-arm tomosynthesis system in accordance with aspects of the present disclosure.

As noted above, and as shown in FIG. 3, the motion of the gantry during the tomosynthesis data acquisition may be referred to as a trajectory, which may consist of multiple orbits (i.e., closed loop or circular movements) of the imager components relative to the patient. For example, an X-ray source may be moved (i.e., have a trajectory) in one or more circular or oval movements (e.g., orbits) in front of the patient, without rotating around the patient, thereby acquiring X-ray projection data over a limited angular range with respect to the patient. That is, in certain embodiments the X-ray source 12 is constrained to move on a first side of the imaged volume and the X-ray detector 14 is constrained to move on a second side of the imaged volume opposite the first side, as shown in FIG. 3. The limited-angle motion traversed by the present tomosynthesis system is in contrast to the spin-type source motion or trajectory typically associated with cone beam computed tomography (CBCT) and computed tomography (CT) type systems and acquisitions.

By way of example, a present implementation relates to the use of a C-arm to perform tomosynthesis imaging in an interventional imaging context. In one such imaging mode, the detector 14 and tube (e.g., source 12) orbit one or more times within respective planes or volumes (e.g., slabs) above and below the table 92. In one embodiment, the orbit generally has a half tomosynthesis angle of 15° to 30° (relative to a reference direction) and an orbit may be traversed in 3 to 8 seconds. In some embodiments, such trajectories may be periodic in that the path traced by the X-ray source may be repeated throughout the examination. Likewise, motion of the imager components along the trajectory may be continuous along a trajectory over the course of an imaging session, even if image acquisition itself is not continuous or is modulated over this time frame.

With the preceding in mind, a tomosynthesis imaging system as shown in FIGS. 1-3 (as well as a bi-plane type system that includes a second imager positioned offset from the first imager 30 and positioned to acquire image data from a different orientation, such as from a lateral perspective) may be used to image a patient as part of a medical procedure, including interventional, surgical, or treatment procedures.

By way of example, a tomosynthesis imaging system as discussed herein may be used in the selection of an optimal location in the arterial tree to administer a pharmacological therapy for treatment of a lesion or tumor downstream from the administration site. To determine the administration site, it may therefore be useful to visualize the arterial tree, the target lesion, and the venous flow downstream from the catheter tip. As noted herein, however, these three separate and different visualizations may each correspond to different points in time as well as different uptake and clearance rates with respect to the administered contrast. For example, for a single ~5 second contrast injection, it can take upwards of a minute for an iodinated contrast bolus to propagate through the arterial, lesion, and venous systems. At any single point in time, only a subset of the vasculature and tissues of interest are maximally opacified. That is, an image taken at a particular time will likely only depict a limited anatomical region, which may or may not be of interest for a given procedure, with full contrast enhancement. As a result, no single acquired image (or no image acquired at a single time) provides the desired visualization information for the procedure.

With this in mind, in accordance with aspects of the present approaches, a global view is generated that integrates the information content of the opacified (i.e., contrast enhanced) anatomic structures over time. In addition, the present approaches may incorporate information pertaining to flow and timing as the contrast bolus propagates through anatomy of interest. These approaches may be particularly useful in a variety of interventional contexts, such as abdominal oncology procedures (where visualization of an arterial phase, a lesion/tumor phase, and a venous phase is useful) and interventional neurology procedures (where temporal imaging for visualizing and evaluating contrast propagation characteristics may be of interest).

With respect to interventional neurology procedures, such procedures may relate to or be concerned with ischemic stroke, aneurysms, and arteriovenous malformations. For example, with respect to ischemic stroke it may be desirable to evaluate perfusion through the parenchyma, which may undergo a relatively long bolus uptake and clearance relative to the arterial and venous phases. These different time constraints, flow rates, and temporal offsets, may make it difficult to develop a useful imaging and visualization for a clinician since visualization of the arterial and venous vasculature and the parenchyma may be desired, but these structures are typically not concurrently opacified. For instance, an iodinated contrast bolus can take upwards of a minute to pass through the arteries initially, the parenchyma, and subsequently the downstream venous systems. Thus, the present approaches allow for 4D (i.e., 3D imaging over time) imaging to allow better visualization of the flow dynamics.

By way of example, in the context of a procedure to treat an aneurysm, thrombus, or embolus, or stenosis there may be a potential of inducing an ischemic or hemorrhagic event (typically downstream of the treatment site). The present approaches may be used to monitor basic perfusion downstream of the procedure site during the procedure and to monitor for perfusion changes. Temporal imaging and visualization as discussed herein makes such monitoring feasible due to the time it takes for the bolus to propagate through the parenchyma. In some embodiments, this may be implemented as a temporally integrated perfusion map that may be used to simplify and/or automate monitoring.

Acquisition:

As discussed herein, temporal imaging and visualization of contrast data into useful visualizations may be accomplished using a variety of techniques that may be implemented at one or more of the data acquisition stage, processing of the acquired projections in the projection domain, processing as part of (or in preparation of) the 3D or 4D reconstruction, and so forth. For example, with respect to the data acquisition stage, the present approaches may benefit from certain functionality provided by the structure and hardware of the imager 30, including, but not limited to, the ability to allow continuous motion of the imager components during a procedure, either in a periodic or varying trajectory.

With this in mind, one adaptation that may be employed during the imaging session is the use of adaptive acquisition, whereby the frame rate and/or other parameters (e.g., mAs, kV, collimated field of view (FOV)) of the acquisition is varied, e.g., based on the progress of the contrast bolus through the anatomic region of interest (or based on other events of interest). In one such embodiment, high image quality and/or three-dimensional (3D) (i.e., volumetric) imaging may not be needed until the contrast bolus is within a given distance (spatially or temporally) to the anatomy of interest. For example, uncertainty may exist as to the timing of the bolus administration and/or the rate or propagation of the bolus with respect to the anatomy of interest and high quality or volumetric imaging may not be needed until the contrast bolus approaches the anatomic region of interest.

Figure 4:
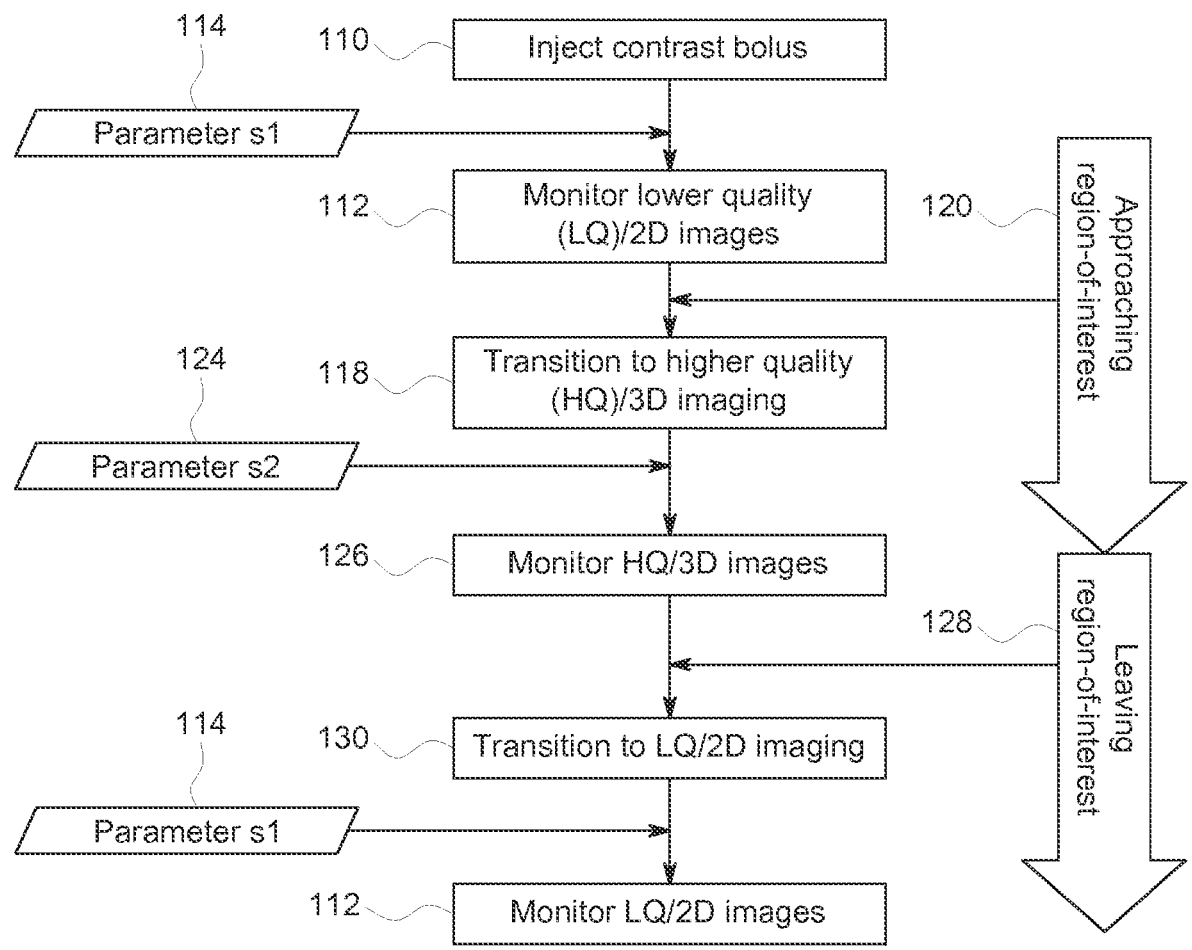
FIG. 4 illustrates a process flow for differential projection or image acquisition, in accordance with aspects of the present disclosure.

In such a scenario, and turning to FIG. 4, a user may take into account the limited need for 3D imaging in the data acquisition process so as to reduce or minimize X-ray dose administered to the patient when 2D or lower quality images are sufficient. For example, after administration (block 110) of a contrast bolus the user may monitor (block 112) 2D projections or other low quality (LQ) images generated using a first set of parameters 114 while the C-arm and source are moved continuously, such as in a defined orbit trajectory. The first parameters 114 may specify one or more of a low frame rate (e.g., approximately 5 frames per second) and/or mAs, kV, or FOV values appropriate for monitoring the progression of the bolus but unsuitable for diagnostic, navigational, surgical, and/or interventional purposes). Based on the observed 2D projections or LQ images, the user may manually initiate (block 118) (such as by toggling a foot pedal or hand control) high quality (HQ) and/or 3D imaging when the contrast bolus approaches (arrow 120) the target anatomy or, more generally, when a process of interest begins. In the depicted example, high quality and/or 3D imaging may be acquired using second parameters 124 that specify one or more of a high frame rate (e.g., approximately 30 frames per second or greater) and/or mAs, kV, or FOV values appropriate for diagnostic, navigational, surgical, and/or interventional purposes).

In the depicted example, the operator may then monitor (block 126) the high quality and/or 3D images to determine when the contrast clears the respective region of interest (arrow 128). At that time, the operator may manually release (block 130) whatever control triggers the high quality and/or 3D image acquisition, thus resuming projection or image acquisition using the first parameters 114 (or other non-HQ parameters) until such time as the contrast bolus is detected approaching another region of interest or until another contrast bolus is administered. Such an approach may be employed multiple times during a given imaging session. For example, the frame rate may be increased as the arterial vasculature of interest is reached by the contrast, decreased after the lesion or tumor of interest is reached, and increased again as the contrast flow enters the venous phase.

Another aspect of the acquisition that may benefit from or be adapted in view of the presently contemplated imager(s) 30 is the availability of repeatable view angles having fixed or constant temporal offsets. For example, to the extent that the motion of the imager components includes (approximately) repeatable orbits that may be traversed in a periodic manner, either as part of a continuous motion trajectory or otherwise, it may be possible to obtain data from repeatable view angles at defined intervals, thus effectively sampling the same regions from the same view angles at fixed (or known) intervals. A conceptualization of this approach can be seen in FIG. 5 where, as a result of acquiring projections (block 150) at set view angles over a repeated trajectory, sets of projections 152A, 152B, 152C, 152D are acquired at each of the respective sampled view angles over time, t. In practice, the number of views may be a function of the orbit time and/or frame rate, where the frame rate may be 15 or 30 frames per second (fps) (or other suitable frame rates), and the orbit time is anywhere between 3 and 5 seconds.

Each of the projections acquired at a given view angle is offset from other projections at that view angle by a fixed time interval (e.g., 3-5 seconds). As discussed in greater detail below, projections acquired in this manner may be useful in visualizing or assessing a given region that undergoes a change between two or more "states" over time, such as may correspond to the presence or absence of contrast (e.g., at a specific location within the anatomy), the presence or absence of an interventional tool, and so forth. Further, based on one or more of the approaches discussed herein, 3D volumes may be reconstructed that are offset in time based on the data acquired at different time intervals. In other embodiments however, and as discussed in greater detail below, the projection data acquired over time may be combined or analyzed so as to produce a 3D image(s) that takes advantage of data acquired at different points in time to produce a higher quality or more informative image.

Further, aspects of the acquisition may be adapted to facilitate temporal integration (or combination) of opacified projections, to control dose to which the patient is exposed, and/or to improve imaging of the anatomic region of interest. By way of example, the field of view of the imager 30 may be positioned or dynamically adjusted, so as to follow or keep centered the region of interest, the contrast bolus, and/or the interventional or surgical tool. In one embodiment this may include adjusting the projection angle by rotating the gantry around one or more of its rotational axes, while in other embodiments this may also include a translational motion, such as of one or more of the imager (or at least one of its components) and/or of the patient table. Similarly, the gantry angle (i.e., the central tomosynthesis angle) may be adjusted (with or without accompanying linear displacement of the patient or imager) to achieve a similar effect.

In addition, the acquisition may be coordinated with one or more concurrently measured physiological measurements (e.g., heartbeat, respiration, and so forth) to allow for patient motion attributable to such physiological activities. By way of example, an orbit may be selected for generating a 3D volume that has the minimum associated patient motion (such as due to respiration). In one embodiment, the frame rate (and/or other parameters of the acquisition process such as kV, mAs, collimated field of view, and so forth) may be adjusted based on the physiological measurements as well. For example, at the onset of a breath hold the system may transition from a low frame rate to a high frame rate (e.g., controlled by a user, as discussed herein above, or automatically, as a function of measured physiological parameters), and the high frame rate may be maintained until a full orbit is traversed. The data acquired during this orbit may then be used to reconstruct a high-quality 3D volume without degradation due to respiratory motion. After the conclusion of this orbit, imaging may continue in a low frame rate mode, therefore allowing for observing the continued process (e.g., to determine the onset of the next phase of interest).

Figure 5:
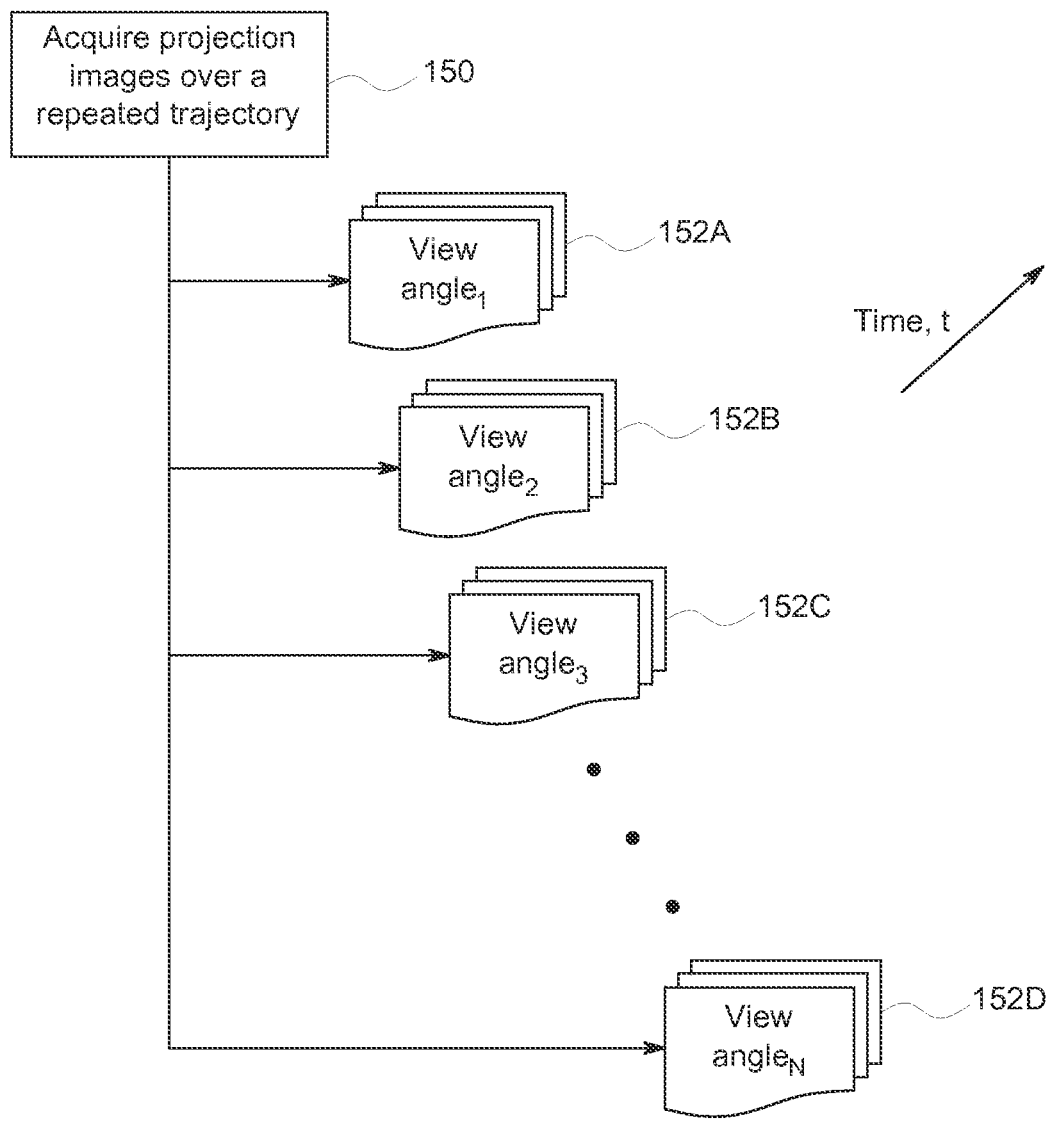
FIG. 5 depicts an acquisition strategy for acquiring projections at a set of repeated view angles over time, in accordance with aspects of the present disclosure.
Figure 6:
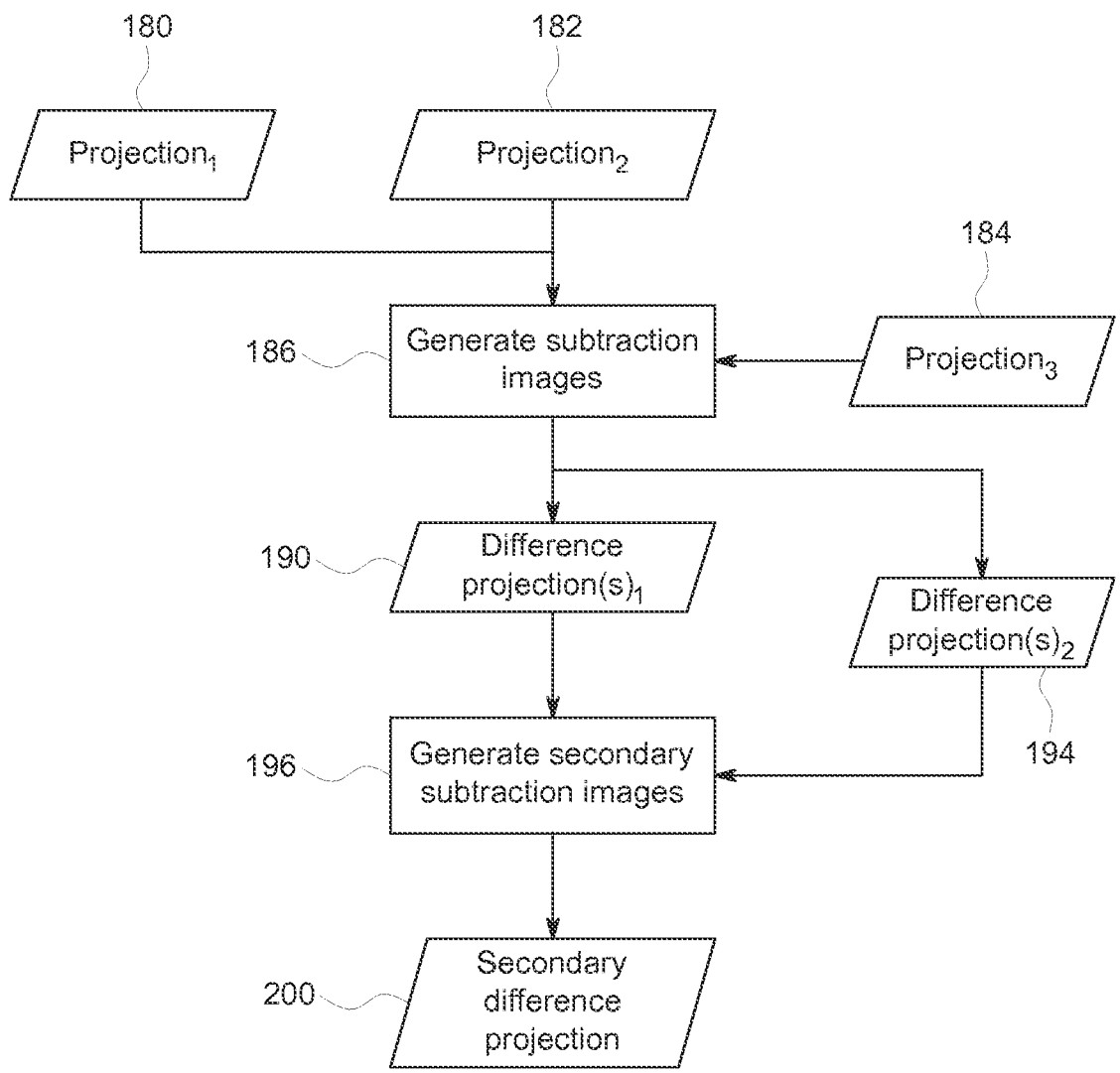
FIG. 6 depicts a process flow for generating difference projections, in accordance with aspects of the present disclosure.

Processing—Projection Domain:

Temporal integration or combination of contrast data into useful visualizations may also be facilitated by various operations performed on the acquired projection data in the projection domain, i.e., prior to backprojection into the 3D image domain, or other 3D volumetric reconstruction approach that generates a 3D volumetric representation of the imaged volume. For example, as noted above, projection data may be acquired using a constant imager motion over a repeated orbit. In such a scenario, the acquired projection data includes, for each view angle, a sequence of images having a constant temporal offset (i.e., each image from that view angle is separated in time by a fixed, constant time interval), as shown in FIG. 5.

As will be appreciated, this is not true for conventional 3D image acquisition with a C-arm, where the imager components instead are moved only once (in a so-called spin, where the source travels on a circular trajectory for about 200-220 degrees around the patient, and the detector travels on a similar circular trajectory opposite to the source, with the center of the circular trajectory being located roughly at the center of the imaged volume), or the spin motion is repeated in a back-and-forth manner. Hence, for projection data acquired by such a back-and-forth rotational or spin motion, acquisitions at a given view angle will typically not occur with a constant temporal offset, but will instead, for virtually all view angles, have non-constant temporal offset (s) that may vary as a function of view angle. For example, for view angles near the end (i.e., reversal point) of a back-and-forth trajectory, two projections at a given view angle may be acquired in quick succession (e.g., with a short temporal offset) as the imager approaches the terminus of the trajectory, acquiring a first projection, reaches the terminus, and then reverses along the trajectory, then acquiring the second projection. Subsequently a longer temporal offset (e.g., substantially greater than the short temporal offset) may pass before the next projection is acquired at that respective view angle as the imager components must traverse the remainder of the trajectory before returning. Further, as will be appreciated, such back-and-forth imager motion is not continuous in that the imager components cease moving at each reversal point on the trajectory.

In contrast, the present approach allows for projection data to be acquired in a continuous manner and with a constant or fixed temporal offset between projections acquired for each respective view angle. This feature of the acquired projections may be leveraged through suitable processing steps in the projection domain, as discussed herein.

By way of example, the acquisition of projections acquired with constant temporal offsets for a given view angle may facilitate subtraction imaging techniques, i.e., where projection data acquired at a first time at the view angle is subtracted from projection data acquired at a second time at the view angle to generate a different projection (and ultimately a different image). In such an embodiment, a first projection acquired at a given view angle at a first time $t_1$ may represent the imaged area in a first state (e.g., non-opacified), while a second projection acquired at the same view angle at a second time $t_2$ (that is offset by a fixed and constant time interval from $t_1$) may represent the imaged area in a second state (e.g., opacified). By subtracting the respective first projection from the second projection, a difference projection based on the opacified vasculature (i.e., a vascular projection) may be acquired which has the static background removed. Note that in some embodiments the image representing the non-opacified state may be acquired after the image data representing the opacified state was acquired (i.e., after the washout of the contrast medium), and the subtraction (or similar processing) may be adapted accordingly.

Figure 7:
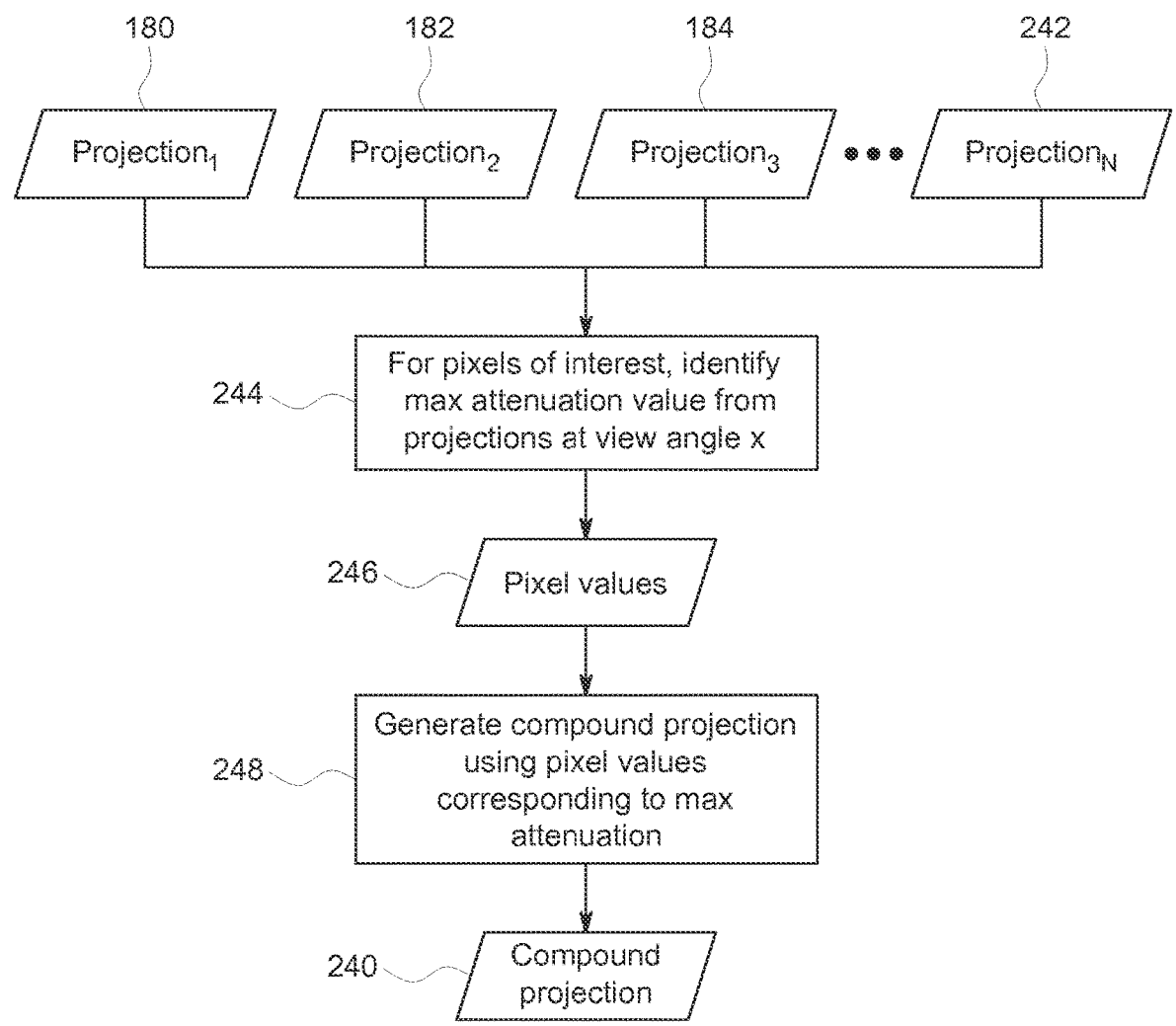
FIG. 7 depicts a process flow for generating compound projections, in accordance with aspects of the present disclosure.

An example of this is shown in FIG. 7, where a first projection 180, taken at a given view angle at time $t_1$ and a second projection 182 taken at the same view angle but at a different time $t_2$ are shown. In this example each of projections 180 and 182 convey X-ray attenuation data for one or more pixels where, for at least some of the pixels, the X-ray attenuation data corresponds to different states (e.g., opacified and not-opacified) in the different projections. For example, first projection 180 may correspond to a region of vasculature that is not opacified while the second projection 182 corresponds to the same region of vasculature viewed from the same view angle but while the vasculature is opacified. In this example, the projection data of first projection 180 may be subtracted (block 186) from the second projection 182 to generate a first difference projection 190. When reconstructed, the first difference projection 190 would generate a difference image, such as a vascular tree without the static background (i.e., with the soft tissue and bone background removed).

Further, as will be appreciated, because projections are being acquired repeatedly at the same view angle (with constant or fixed temporal offset in certain embodiments), the subtracted projections (e.g., difference projection 190) generated with respect to two times (e.g., $t_1$, $t_2$ and $t_2$, $t_3$) may themselves be used in additional subtractive operations (block 196), which may provide information about the change in the uptake (or opacification) rate with respect to the known, constant time interval. For example, a first difference projection 180 corresponding to opacified vasculature may be subtracted from additional difference projections 194 generated using the subsequent projections 184 to assess the difference in the contrast uptake rate over times $t_1$, $t_2$, and $t_3$ while still removing the static background. Such a secondary difference image 200 may be used as a "higher order" (i.e., "uptake acceleration or deceleration" or change-of-uptake-rate) image and may convey useful information about the temporal characteristics at which contrast is taken up and/or washed out of a given anatomic region or structure. Similarly, additional parameters characterizing the uptake/washout may be generated from two or more images acquired at the same view angle. These parameters include, e.g., peak time, FWHM, and so forth.

In another embodiment, images from the same view angle acquired at 2 or more time points (with constant or fixed temporal offset between time points in certain embodiments) may be used to estimate the corresponding image values at time points in-between the ones that were actually acquired. For example, using a linear model, an image for a given view angle at a certain time point t can be estimated from the images acquired at $t_1$ and $t_2$. In some embodiments, $t_1$ and $t_2$ may be selected to be the time points at which image data for the considered view angle was acquired immediately before and immediately after time point t, respectively. Higher order models, or other interpolation techniques may be used as well. For example, data acquired at 3 or more time points generally allows estimation of the time and value of the highest opacification (peak opacification) for any pixel location in an image, e.g., by using a suitable quadratic or higher order polynomial as model for the temporal evolution. In one embodiment the interpolation scheme may vary from pixel to pixel. For example, for some pixels (which may be representative of slow contrast uptake/washout, e.g., as observed in soft tissue/parenchyma) an interpolation may be based on a linear model, using only data from two projections, while for some other pixels (which may be representative of a fast bolus uptake/washout, which may be representative of arteries/veins) the interpolation may be one-sided (e.g., using only data collected before, or only data collected after), or may be based on a higher order model, employing data from 3 or more projections.

In addition to subtraction imaging, the acquisition of projections at repeated view angles allows for the generation of compound projections using projection data acquired over time (i.e., over multiple orbits) as discussed herein. Projection processing in such an approach may be synchronized with the gantry phase or motion. Turning to FIG. 7, for a given view angle one or more compound projections 240 may be generated by identifying a pixel value corresponding to maximum attenuation 246 for pixels of interest (e.g., pixels corresponding to vasculature or tissue of interest) from among the projections 180, 182, 184, 242 acquired at the respective view angle. Depending on the implementation, the maximum attenuation value may correspond to either the maximum or the minimum intensity observed for a pixel in question from among two or more projections of the set of projections. For example, if detector data (i.e., before negative (−) log conversion) is being processed, the minimum intensity represents peak opacification of the contrast agent whereas maximum intensity represents minimum opacification. Conversely, after negative (−) log conversion, the maximum intensity represents peak opacification of the contrast agent whereas minimum intensity represents minimum opacification.

In certain embodiments, as noted above, the projections 180, 182, 184, 242 may be acquired at a fixed or constant time interval. As depicted in FIG. 7, the selected pixel values 246 corresponding to maximum attenuation from among the available temporally offset projections 180, 182, 184, 242 are combined (block 248) in a synthesized projection to generate a compound projection 240. That is, in this example, at each pixel location, the corresponding value corresponding to peak attenuation from among the available projection images is selected to represent the pixel value in the compound image at that pixel location. The resulting compound projection 240, in the case of a vasculature representation, depicts the maximally opacified vascular structure, without the ebbs and flows of contrast that actually occur over time during the acquisition of the projections 180, 182, 184, 242. A set of compound projections 240 (e.g., a set of compound projections corresponding to a set of view angles representing a full orbit) may be reconstructed to generate an image or volume based on the maximum observed opacity values over the time frame used to generate the compound projection 240. In certain embodiments, the structure of interest alone (e.g., the vasculature, lesion, soft tissue, and so forth) may be reconstructed from the compound projections 240, effectively using the best observed (or interpolated, as discussed below) values over the course of the examination (i.e., over time). This is in contrast to approaches where an image of a structure of interest is reconstructed from data acquired over a single trajectory traversal, where during that single trajectory traversal only a part of the vasculature of interest may be opacified.

Such a compound imaging approach may be useful in instances where a bolus (or boluses) are administered which are "short" in duration (i.e., are taken up and cleared quickly or constitute a relatively limited quantity of administered contrast) with respect to the anatomy in question. Such short boluses may result in only a limited portion of the vasculature being opacified as the bolus uptake and washout occur in rapid succession as the bolus propagates through the vasculature. Thus, for a given view angle where projections are acquired at different times (e.g., projections 180, 182, 184, 242), a different portion of the vasculature or tissue may be opacified which is downstream from the previously opacified vasculature or tissue due to the rapid propagation of the contrast bolus. In this approach, the compound imaging would capture the maximum attenuation for each pixel in each view angle over time to provide a complete volume of the vasculature. In certain embodiments, such an approach may further benefit from an interpolation (as discussed below) to estimate peak opacification values in cases where the peak opacification may occur at times when no actual image data was acquired.

By way of further example, in certain embodiments processing for each pixel may be adapted to the characteristics of the contrast uptake/washout at the corresponding location. For example, bolus duration may be taken into account to provide some degree of stratification or informational refinement. In one such embodiment, for a long duration bolus within a tissue, where substantial opacity information may be present within all or part of a set of multiple projections, a maximum attenuation may be determined or derived from among some or all of the acquired projections. That is, a useful data point for each pixel may be assumed to be present within the relatively large number of available projections.

Conversely, in situations where the bolus duration is relatively short, as discussed above, the limited number of relevant projections may contain certain of the peak attenuation pixel values, but not others (where the peak attenuation does not coincide with the acquisition time of the projections). In such an instance (and as discussed herein), pixel values corresponding to peak attenuations occurring at times between those of the available projections may be estimated or interpolated using a model (e.g., a model taking into account one or more of contrast propagation rates, physiological uptake, physiological clearance, and so forth).

Further, in some embodiments bolus duration (or maximum rate of change in contrast, or similar suitable parameters) may be used to differentiate between tissue types, such as between vasculature and surrounding tissue. For example, pixel values for peak attenuation may only be selected for regions in which opacity changes rapidly (i.e., short bolus locations), which will likely correspond to vasculature. In such an embodiment, pixels corresponding to fast moving contrast (i.e., short bolus) may have intensity values set based on the intensity values observed corresponding to peak attenuation or using estimated peak attenuation intensities, as described herein. Conversely, pixels that do not correspond to the passage of the short duration bolus may be set to an arbitrary or background value, such as zero.

Further variations on the compound imaging approaches discussed above may be employed. For example, compound projections 240 may be generated using one or more of the difference projections 190, 194, 200 described above (as opposed to measured projections 180, 182, 184, 242). In such an implementation, the resulting compound projection may represent the maximum slope (i.e., rate of change) of contrast related opacity over time. Such a compound image 240 would thereby effectively depict the maximal contrast uptake or washout over time (e.g., per unit time) for a given anatomic region, which may be of interest.

Figure 8:
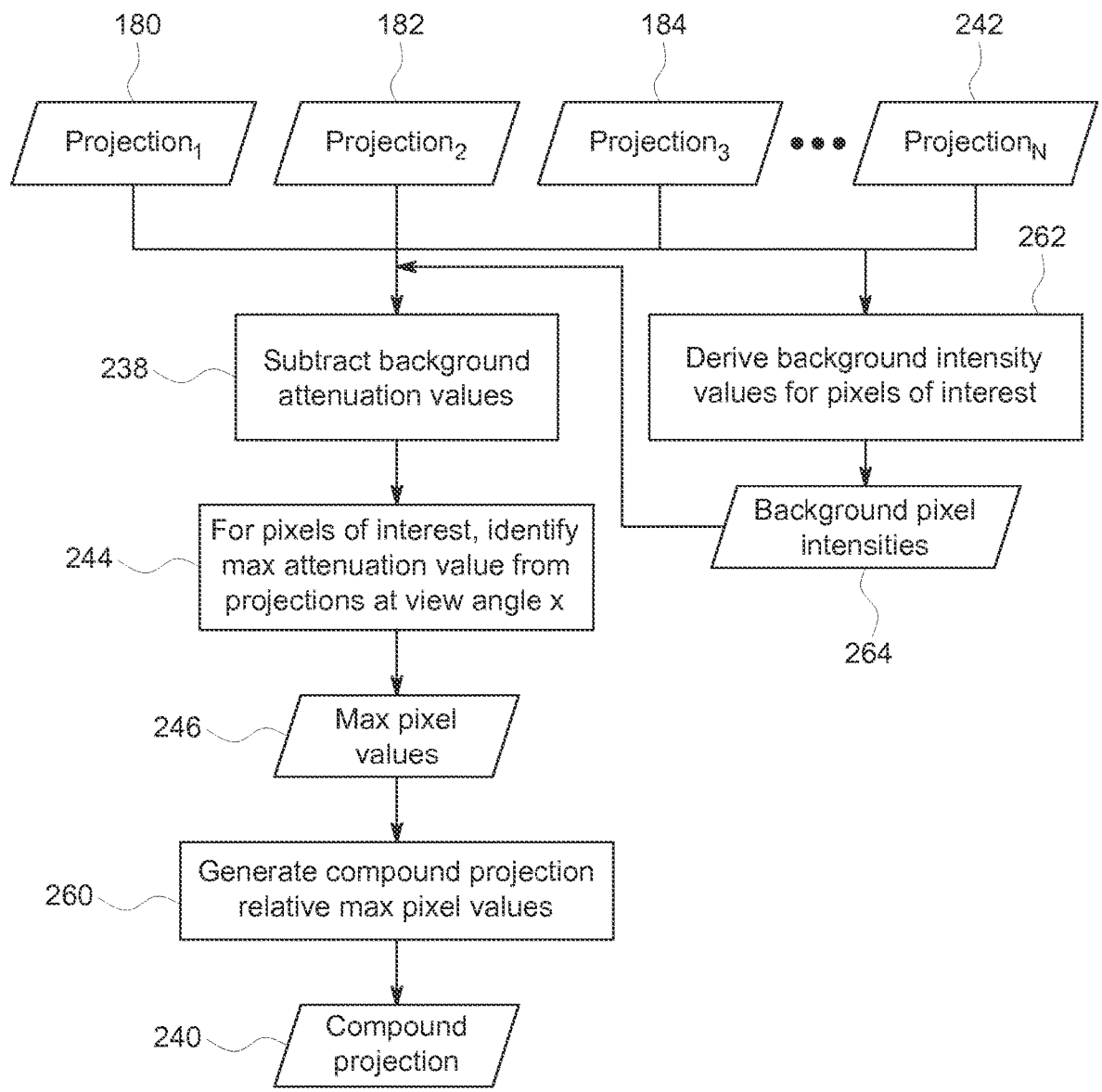
FIG. 8 depicts a further process flow for generating compound projections, in accordance with aspects of the present disclosure.

Similarly, in another embodiment multiscale processing (or a comparable processing approach) may be employed to derive the maximum attenuation relative to the background structures (i.e., the maximum relative opacity), as opposed to using the observed or raw maximum attenuation. That is, the maximum relative intensity value associated with a given pixel at a given view angle corresponds to the raw pixel value with the background intensity contribution subtracted. By way of example, and turning to FIG. 8, the projections 180, 182, 184, 242 may be processed to derive (block 262) background intensity values 264 for the pixels of interest. By way of example, multiscale processing may be used to derive the local background attenuation (which is given, e.g., by the attenuation of the contrast-medium traversing the parenchyma) at any given vessel (artery or vein) location, where the vessels/vasculature are generally associated with small, high attenuation structures in the image. The background pixel intensities 264 so derived may be subtracted (block 238) from the associated attenuation values observed at vessel locations (thereby obtaining a value representing the relative attenuation of the vessel over the background) to derive the pixel values adjusted or normalized for background contribution. These adjusted pixel values may then be used (block 244) to identify, for pixels of interest, the pixel values 246 associated with maximum attenuation. These observed pixel intensities 246 may then be used to generate (block 260) a compound image 240 corresponding to the relative maximum or minimum intensity values (depending on whether the negative (−) log conversion has been performed) for the pixels or regions of interest. In this manner, in one embodiment the intensity of the vascular tree depicted in an image generated from such a compound projection 240 will reflect the separate contribution of the opacified vessels alone, without contribution attributable to the background tissue attenuation. As mentioned above, a multi-scale (or similar) approach may be used to generate the maximum relative attenuation value for vasculature, where additional knowledge about the small size of the vessels, maybe combined with assumptions about repeatable position of vessels in the projection images (since the gantry trajectory is repeatable) and temporal smoothness, as well as the fact that additional attenuation due to a contrast medium can never be negative, may be used.

While certain of the preceding examples utilize either the relative or absolute observed maximum opacity values (i.e., pixel values), in other embodiments interpolation techniques may be employed to derive intensity values at a given view angle for one or more pixels. Implementing such interpolation techniques may be facilitated by the fixed temporal offset between projections acquired at a given view angle in accordance with the present techniques, which allows interpolation to intermediary time points, for which no projection data was directly observed, to be performed.

Figure 9:
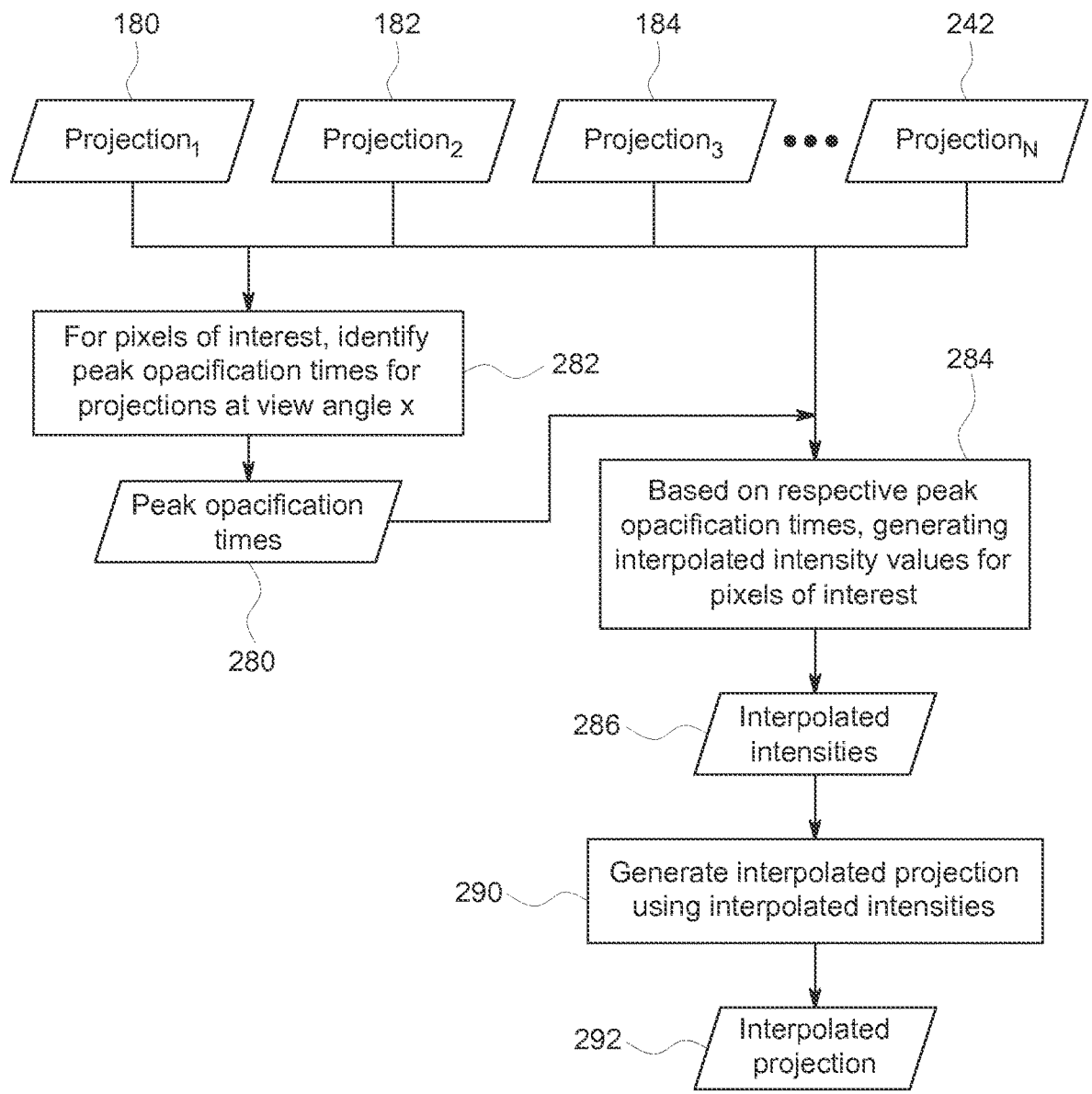
FIG. 9 depicts a process flow for generating interpolated projections, in accordance with aspects of the present disclosure.

By way of example, and turning to FIG. 9, a pixel value (i.e., intensity) for a given pixel may be interpolated based on a time of interest (such as a "peak opacification time" 280 that presumably falls between two of the temporally offset projections 180, 182, 184, 242, acquired at a given view angle (or otherwise outside the temporal range of these projections) for the pixel in question. Thus, in this example, a time 280 is estimated (block 282) for a given pixel at which the pixel likely experienced peak opacity and which falls between the times at which projection data was acquired for the pixel at the view angle in question. Thus, for a given view angle, a given time corresponding to peak opacity is identified for each pixel. In one embodiment, joint estimation of peak time and peak opacification, e.g., by using a fit of the data points with a quadratic polynomial may be used. The peak time and peak value of this polynomial provide the sought-for parameters. In other implementations, the time of interest may correspond to other events or may simply correspond to an arbitrary designation by the reviewer, essentially allowing the reviewer to "freeze time" over a set of projections used in the 3d reconstruction.

Based on this time 280, and the intensities observed in the temporally proximate acquired projections (e.g., projections 182 and 184), the respective pixel intensity 286 can be estimated (block 284) (e.g., interpolated) for the peak opacification time 280 (or other time of interest) determined for the pixel in question. Interpolation of the pixel intensity 286 at the time of interest (e.g., estimated peak opacification time 280) may be performed using either a one-sided (i.e., using only data on one side of the peak opacification time 280) or a two-sided (i.e., using data from both sides of the peak opacification time 280) approach. The respective interpolated intensities 286 may be used to generate (block 290) a synthetic projection, e.g., an interpolated projection 292 that may then be reconstructed to generate a viewable 3D volumetric image. When interpolating to a peak opacification, the reconstructed volume represents the vasculature at the respective peak opacification intensity values.

As noted above, while the preceding discussion addresses creating an interpolated projection image where each pixel value corresponds to the peak opacification at that pixel—and in particular to the attenuation at the time of peak opacification for that pixel (which may be different for each pixel), the interpolation approach as discussed here may also be used to generate interpolated projection images that represent a projection view at any time point (i.e., not just at the estimated time corresponding to peak opacification) where no projection data (for that view angle) was directly observed. In one such embodiment, when interpolating to a single fixed point in time, such an approach may be used to reconstruct a pseudo-static volume image at that single time point (where this dataset is reconstructed from a set of pseudo-static projection images, i.e., projection images at different view angles that were all generated by interpolating to the same time point). Similarly, the present approach may be used to generate a temporal sequence of pseudo-static volumes, which may then be used to derive temporal characteristics of contrast uptake and washout, for different locations within the volume. As discussed above, this interpolation may be one-sided or two-sided, and may vary from pixel to pixel, e.g., based on the temporal characteristics (e.g., rate of change) at each pixel. In one embodiment, the interpolation for at least a subset of pixels is based on the corresponding pixel value in three or more projection images at that view angle. In one embodiment, the specific interpolation approach used at a given pixel depends on the temporal characteristics observed at that pixel.

In certain embodiments, different interpolation schemes may be applied to different portions of an image, such as to different types of anatomic regions represented in a projection or image reconstructed from the projection. For example, blood vessels may be associated with faster contrast propagation (i.e., a short bolus duration corresponding to rapid uptake and clearance) and may benefit from a one-sided interpolation scheme. Conversely, non-vascular organs or tissues, which may take up and clear the contrast more slowly (i.e., long bolus duration), may benefit from a two-sided interpolation scheme. Thus, such different anatomic regions and/or structures may be automatically or manually identified, segmented, and/or labeled, and the appropriate interpolation scheme applied.

Further, in certain implementations the interpolation that is performed may be iteratively updated, such as in response to newly acquired projections (e.g., Projections$_N$ 242) at the view angle in question. For example, interpolated pixel values (i.e., intensities 286) at the view angle in question may be derived after some specified number of projections (e.g., projections 180, 182, 184) are acquired at the view angle in question. As additional projections (e.g., projection(s) 242) are acquired at the view angle, the peak opacification time 280, and corresponding interpolated pixel values 286, may be updated or regenerated (i.e., calculated from scratch) based on the newly acquired projections 242. Such an iterative approach may provide a better estimate of the time 280 when peak opacification occurs for the location or pixels in questions. Better estimation of the peak opacification times 280 will then presumably translate to better interpolation values 286. Similarly, joint estimation of peak opacification time, and peak attenuation (e.g., using a parametric model, for example a quadratic polynomial) would yield improved results. Depending on the implementation, such an iterative approach may be based on the aggregated projection data for the view angle in question (i.e., all of the acquired projections at that view angle or all of the projections at that view angle in which contrast is present) or upon a moving window of projections (e.g., the most recent 4, 6, or 8, projections).

As will be appreciated, multi-scale processing as discussed above may also be employed in conjunction with approaches so as to remove background structures (e.g., large background structures) from consideration. Further, registration of the projections used in the interpolation process for a given view angle may be performed so as to address patient (or other) motion.

With the preceding in mind, the compound and/or interpolation processing approaches may be used to extract or otherwise generate perfusion curves for a subset of the projection images acquired at the same view angle with fixed or known temporal offsets. Such curves may be generated for different regions in the image corresponding to different parts of the anatomy, or they may be generated on a pixel-by-pixel basis. Such curves may be used to illustrate the evolution or progression of the perfusion over time based on the observed contrast progression over the known time intervals of the projection images. In addition, characteristic parameters of the perfusion process may be extracted from a sequence of (directly acquired, interpolated, compounded, or otherwise generated) projection images. Such parameters may include peak opacification, peak opacification time, FWHM (full-width half-max), and so forth. With the preceding discussion in mind, various enhancements of 4D (i.e., 3D in time) reconstructions may be provided that utilize certain of the above described acquisition and processing features. In one embodiment, projection images may be generated for a fixed point in time (e.g., using an interpolation approach as discussed above), and a 3D volume providing a 3D "snapshot" of the volume at that instant in time may be generated. By using this approach for a suitable sequence of time points a 4D sequence (i.e., a temporal sequence of 3D volumes) may be generated, from which, for example, perfusion characteristics at different regions in the volume may be extracted (or a 3D compound image may be created, etc.).

In another embodiment, the generated projection images (e.g., compound and/or interpolated projection images, for multiple view angles) may be used to reconstruct one or more 3D or 4D volumes, and similar curves and/or parameters may be generated for different regions or voxels within the imaged volume.

It should also be appreciated that, in certain embodiments, compounding of data may be performed in 3D, such as to reconstruct high-contrast vasculature, using data acquired from different orbits (which may or may not overlap). That is, vessels may be reconstructed in three-dimensions to form a complete vessel tree. In such embodiments, the orbits along which projection data are acquired need not be the same (i.e., may not be repeatable orbits). Further, hierarchical multi-scale three-dimensional reconstruction approaches may be extended so as to encompass the addition of a temporal element (or other suitable approaches may be used). Such approaches provide improved image quality in tomosynthesis imaging, including reduction of streaks and out-of-plane artifacts. These approaches selectively emphasize certain aspects (such as features corresponding to different image scales or frequency bands) of the projection or image data during iterations of a reconstruction process. In this manner, during a multi-stage reconstruction process, different image features may be refined or emphasized during a given stage while other features (e.g., artifacts or noise) may be deemphasized or removed. Such an approach is suitable for reconstructing small structures, such as vasculature and devices, with reduced, minimal, or no blurring. Due to this approach, the reconstruction of the background (e.g., the anatomy surrounding these small structures) is also minimally impacted by artifacts due to out-of-plane structures, as are common with conventional reconstruction algorithms employed in tomosynthesis imaging.

By way of example, in accordance with certain embodiments, a multi-stage, iterative approach for tomosynthesis reconstruction is employed. In such embodiments, the reconstruction process may be broken down into two or more stages, each of which are directed to selectively emphasizing different aspects of image quality or detail (such as selectively emphasizing features or structures corresponding to different image scales or frequency bands). In such an implementation, each stage can, correspondingly, employ different parameters or ranges of parameters (e.g., weights, thresholds, criteria) during that stage of the iterative reconstruction. With this overall multi-stage framework in mind, each iteration step of the reconstruction: (a) creates modified projection images, such as by processing or preparing either the projection data (in an initial iteration) or the residual projection data; (b) backprojects the modified projection images to create an image volume update for the current estimate of the image volume; (c) creates a modified image volume update for the current iteration; (d) adds (or otherwise combines) the modified image volume update to the current image estimate to form an updated estimate of the image volume; (e) re-projects the updated estimate of the image volume; and (f) creates residual projection images for use in the next iteration. The iterated steps may be repeated until a completion criterion is met for a given stage (e.g., a cost function is minimized or an empirically determined number of iterations have been performed (e.g., 10-200 iterations)) before proceeding to the next stage or, if in the final stage, concluding the reconstruction. Since certain implementations of the reconstruction approach as disclosed herein operate in multiple stages, each stage may have its own stopping criterion (e.g., number of iterations).

With respect to the creation of the modified projection images, in certain implementations this may be accomplished by multi-scale or frequency band processing. Creation of the modified projection images may also involve thresholding and/or clipping of the projection images and/or the application of positivity constraints. Similarly, in certain embodiments, creation of the modified update volume may involve one or more of thresholding, clipping, application of a positivity constraint, constraining to a support region, and/or scaling of the update volume.

With this in mind, an extension of such a multi-scale 3D reconstruction approach may incorporate temporal information derived from the present approaches. For example, in such an approach fine-scale, high-contrast data may be processed and reconstructed first. This may involve, for example, multi-scale processing and backprojection, where in the 3D image domain initially (in an iterated process) only large values are retained, where the determination whether a value is considered to be "large" is made not only in the spatial domain, but also over time. In this way, small structures (e.g., vessels) are reconstructed first, at their respective peak opacification. In accordance with the present approach, the high-contrast data initially processed in one such multi-scale approach may be taken or derived across time, such as from projection data acquired over (or interpolated from) fixed intervals as discussed herein. In such an approach, a parametric model may be employed at each voxel. Further, in such approaches, the projection data may or may not be acquired over repeated trajectories.

In certain implementations, labels for identifiable regions may be generated or reconstructed, where the labels may be assigned, e.g., based on the temporal characteristics observed in the projection data (e.g., peak opacification, FWHM, etc.). As will be appreciated, such labeling operations typically rely on characteristics within an image (e.g., threshold intensities, identified edges and boundaries, shape or geometric analysis, and so forth) to identify and correspondingly label structures (e.g., vasculature, bone, soft tissue/parenchyma, devices/tools, background, indeterminate) within the reconstructed image to facilitate review by a clinician.

Temporal information available in the present embodiments, such as due to the availability of projections acquired at constant, fixed time intervals for a given view angle, may be used in the label assignment process. For example, temporal characteristics related to observed opacity may be used to determine the nature of the region in question (e.g., arterial vasculature, parenchyma, venous vasculature, and so forth) based on known or expected temporal characteristics for such regions (such as parametric perfusion curves modeling contrast uptake and/or washout over time) and labels assigned accordingly. Thus, in one embodiment, a volume to be labeled may have various, suitable temporal characteristics defined for the volume to facilitate the labeling process. In such an embodiment, a label volume may be identified based on one or more temporal characteristics for that region including, but not limited to: peak opacity time, full width at half maximum (FWHM), slope (i.e., uptake/washout rates), maximum contrast, and so forth. Prior information or knowledge (such as that bone will not vary over time) may also be used in the labeling process.

In such a manner, a 3D volume consisting of labelled voxels may be generated (e.g., by reconstructing a label volume from labelled projection images, or by assigning labels to a previously generated 4D volume). In a further step, temporal characteristics (e.g., attenuation values, maybe corrected for pathlength etc.) may be assigned to the labelled voxels. In one example, only two labels may be used, one for vasculature, and one for background. Based on the 3D reconstructions at different points in time, a label map representing the imaged vasculature may be generated (although different parts of the vasculature may be maximally opacified at different points in time). In one embodiment, such a label map may be generated based on a volumetric reconstruction that is based on subtracted projection images, or subtracted compound images, which contain only the opacified vasculature, as discussed herein above. The known locations of the vasculature in the 3D volume may then be populated with their associated temporal sequence of attenuation values, where these attenuation values may be extracted from the collected sequence of projection images. This represents now a 3D label image (volume representing the vasculature) that has been augmented with temporal information about the contrast propagation (over time) through the vasculature. In one example, the location of a point on the 3D vasculature in each projection image is determined, and the relative attenuation (of that location in the projection image, relative to the background) is assigned to the location on the vasculature. Since the relative attenuation varies over time, a temporal sequence of augmented label maps may be generated, showing the ebb and flow of the contrast within the imaged vasculature. Due to the continuous nature of our acquisition, in one embodiment this temporal evolution may show the propagation of the contrast medium through the vasculature over a period of 15 seconds or more. In this manner, a temporal evolution of the opacification of the vasculature, sampled at the same rate as the original frame rate at which projection images were acquired, is generated. In one embodiment, this allows for visualizing the ebb and flow of the contrast at sampling rates much higher than, for example, the orbit time (which is 3-5 seconds), or the heart rate (which will drive the propagation of the contrast medium through the vasculature)

Temporal characteristics, in addition to being used in the labeling process, may also be displayed or made available to a clinician reviewing the augmented labeled volume. In one embodiment, similar temporal characteristics may also be overlayed onto the background (e.g., soft tissue/parenchyma), where the values for the parenchyma may be generated from multiple reconstructed 3D volumes (where the time constant for generating those volumes is adapted to the slower (when compared to the vasculature) temporal characteristics of the associated tissue.

In certain embodiments, additional projection data acquired using a second, concurrently operated, imager (operated at a different orientation with respect to the patient) may be incorporated so as to add additional projection data to the processing steps as discussed herein. Such a second imager may be operated in a bi-plane configuration, as discussed herein.

Further, it should be appreciated that in certain circumstances it may be useful to fuse volumes or images generated using the present approaches with pre-operation (i.e., pre-op) image data, such as data acquired using magnetic resonance imaging (MRI), computed tomography (CT), or other modalities for planning or diagnostic purposes. For example, there may be instances where the contrast resolution for the 4D imaging approaches discussed above is insufficient to capture all structures of interest. In such instances, the structures of interest may be derived from the pre-op images and synthetically added to the images generated using the present 4D approaches. The location of the structures of interest may be determined via registration of the vasculature (or other suitable high-contrast structures) between two separate imaging sets.

Technical effects of the invention include the acquisition of projection data using a C-arm system and the processing of such data based using temporal aspects of the imaged volume, such as the uptake and clearance of a contrast agent within the volume. Such temporal aspects may be used in the acquisition process, such as to differentially acquire images based on the propagation of the contrast agent. In addition, such temporal aspects may be used in the processing of projection data to generate differential projections (e.g., first or second order subtraction projections), compound projections synthesized using the absolute or relative maximum opacity values observed over time for a region of interest, or interpolated projections synthesized using observed opacity values at known or fixed time intervals and a derived peak opacity time.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of acquiring X-ray projection data, comprising:
   during an imaging session, continuously orbiting an X-ray source and an X-ray detector of a tomographic imaging system within a limited angular range with respect to an imaged volume, wherein the X-ray source is constrained to move on a first side of the imaged volume and the X-ray detector is constrained to move on a second side of the imaged volume opposite the first side;
   prior to an event of interest, acquiring projection data at one or more of a first frame rate, a first operating current, a first operating voltage, or a first field-of-view using the X-ray source and the X-ray detector while orbiting the X-ray source and the X-ray detector through one or more orbits; and
   subsequent to the event of interest, acquiring projection data at one or more of a second frame rate, a second operating current, a second operating voltage, or a second field-of-view using the X-ray source and the X-ray detector while orbiting the X-ray source and the X-ray detector through the one or more orbits.

2. The method of claim 1, wherein the event of interest is based on a distance of a contrast bolus from an anatomic region of interest, a rate of change of the contrast bolus, a propagation rate of the contrast bolus, or a respiratory state of a patient.

3. The method of claim 1, comprising:
   subsequent to a second event of interest, wherein the second event of interest is one or more of a contrast bolus exiting an anatomic region of interest, completion of an orbit of the X-ray source and X-ray detector, completion of a fixed time-interval, or an operator input, acquiring projection data at one or more of the first frame rate, the first operating current, the first operating voltage, or the first field-of-view again.

4. The method of claim 1, wherein prior to the event of interest, the projection data is acquired at the first frame rate that is less than or equal to 15 frames per second, and subsequent to the event of interest, the projection data is acquired at the second frame rate that is 30 frames per second or greater.

5. The method of claim 1, wherein the projection data acquired prior to the event of interest is processed to generate two-dimensional images and wherein the two dimensional-images are displayed to an operator who commands acquisition of the projection data at one or more of the second frame rate, the second operating current, the second operating voltage, or the second field-of-view when the first event of interest occurs.

6. The method of claim 1, wherein the projection data acquired subsequent to the event of interest is reconstructed to generate three-dimensional images and wherein the three dimensional-images are displayed to an operator who commands acquisition of the projection data at one or more of the first frame rate, the first operating current, the first operating voltage, or the first field-of-view subsequent to a second event of interest.

7. The method of claim 1, wherein the first frame rate, the first operating current, or the first operating voltage are suitable for generating two-dimensional images showing the first event of interest and the second frame rate, the second operating current, or the second operating voltage are suitable for generating three-dimensional images suitable for medical diagnosis or tool navigation within the imaged volume.

8. The method of claim 1, further comprising moving a patient support table during acquisition of at least a portion of the acquisition data.

9. A method of processing projections, comprising:
during an imaging session, continuously orbiting an X-ray source and an X-ray detector of a tomographic imaging system within a limited angular range along an orbital path with respect to an imaged volume, wherein the X-ray source is constrained to move on a first side of the imaged volume and the X-ray detector is constrained to move on a second side of the imaged volume opposite the first side;
acquiring projection data using the X-ray source and the X-ray detector while orbiting the X-ray source and the X-ray detector in the orbital path and relative to the imaged anatomy, wherein the acquisition of projection data yields projection images of the imaged anatomy in two or more states; and
generating one or more three-dimensional images adapted to the dynamic nature of the imaged object, wherein the generating of the three-dimensional images is adapted based on one or more of selection of a time window for reconstruction, generation or use of compound or interpolated projections, separate reconstruction of structures within the three-dimensional images, or temporal evolution of at least one category of structure.

10. The method of claim 9, wherein the time window for reconstruction is selected based on one or more of contrast bolus location, contrast bolus propagation, contrast bolus rate of change, respiration state of a patient, or an estimated time of maximum attenuation of at least a portion of a structure of interest.

11. The method of claim 9, wherein the separate reconstruction of structures within the three-dimensional images is based on one or more anatomic labels applied to voxels of the three-dimensional images.

12. The method of claim 9, wherein the X-ray source and X-ray detector traverse two or more orbits along the orbital path.

13. The method of claim 12, wherein a temporal evolution of at least one category of structures has a faster dynamic than the orbit time.

14. A method of generating a compound projection, comprising:
during an imaging session, continuously orbiting an X-ray source and an X-ray detector of a tomographic imaging system within a limited angular range along an orbital path with respect to an imaged volume, wherein the X-ray source is constrained to move on a first side of the imaged volume and the X-ray detector is constrained to move on a second side of the imaged volume opposite the first side;
acquiring projection data using the X-ray source and the X-ray detector while orbiting the X-ray source and the X-ray detector in the orbital path and relative to the patient table, wherein at least a set of projections are acquired at the same view angle at different times;
for one or more pixels of interest depicted in the set of projections, determining a pixel value corresponding to a maximum X-ray attenuation among two or more projections of the set of projections; and
generating a compound projection using the pixel values for the pixels of interest.

15. The method of claim 14, wherein the orbital path comprises a half tomosynthesis angle of 15° to 30° relative to a reference direction.

16. The method of claim 14, comprising:
deriving a background intensity value within each projection image for each pixel of interest; and
subtracting the background intensity value for each respective pixel of interest before determining the maximum X-ray attenuation value for the corresponding pixel of interest when generating the compound projection.

17. A method of generating an interpolated projection, comprising:
during an imaging session, continuously orbiting an X-ray source and an X-ray detector of a tomographic imaging system within a limited angular range along an orbital path with respect to an imaged volume, wherein the X-ray source is constrained to move on a first side of the imaged volume and the X-ray detector is constrained to move on a second side of the imaged volume opposite the first side;
acquiring projection data using the X-ray source and the X-ray detector while orbiting the X-ray source and the X-ray detector in the orbital path and relative to the patient table, wherein at least a set of projections are acquired at the same view angle at different times;
determining a time of interest for each of one or more pixels of interest depicted in the set of projections;
based on the time of interest for each pixel of interest, determining an interpolated intensity for each pixel of interest using two or more respective projections from the set of projections;
generating an interpolated projection using the interpolated intensities for the pixels of interest.

18. The method of claim 17, wherein each projection in the set of projections is temporally offset by a fixed time interval.

19. The method of claim 17, selecting, on a pixel-by-pixel basis, an interpolation approach for each pixel based on temporal characteristics observed at each respective pixel, wherein the interpolation approach may be different from pixel to pixel.

20. The method of claim 19, wherein determining the interpolated intensities utilizes a one-sided interpolation approach or a two-sided interpolation approach.

21. The method of claim 17, wherein the time of interest comprises one of a time of peak attenuation for each pixel of interest or a pre-determined point in time.

* * * * *